(12) United States Patent
Hergenrother et al.

(10) Patent No.: US 10,350,207 B2
(45) Date of Patent: Jul. 16, 2019

(54) PAC-1 COMBINATION THERAPY

(71) Applicant: The Board of Trustees of the University of Illinois, Urbana, IL (US)

(72) Inventors: Paul J. Hergenrother, Champaign, IL (US); Jessie Peh, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/579,689

(22) PCT Filed: Jun. 6, 2016

(86) PCT No.: PCT/US2016/036063
§ 371 (c)(1),
(2) Date: Dec. 5, 2017

(87) PCT Pub. No.: WO2016/197129
PCT Pub. Date: Dec. 8, 2016

(65) Prior Publication Data
US 2018/0161326 A1 Jun. 14, 2018

Related U.S. Application Data

(60) Provisional application No. 62/171,882, filed on Jun. 5, 2015, provisional application No. 62/345,629, filed on Jun. 3, 2016.

(51) Int. Cl.
*A61K 31/506* (2006.01)
*A61K 31/495* (2006.01)
(Continued)

(52) U.S. Cl.
CPC .......... *A61K 31/506* (2013.01); *A61K 9/0019* (2013.01); *A61K 9/12* (2013.01);
(Continued)

(58) Field of Classification Search
CPC .. A61K 31/555; A61K 31/506; A61K 31/495; A61P 35/00
(Continued)

(56) References Cited

U.S. PATENT DOCUMENTS 8,592,584 B2 11/2013 Hergenrother et al.
8,778,945 B2 7/2014 Hergenrother et al.
(Continued)

FOREIGN PATENT DOCUMENTS

WO 2006128173 A2 11/2006
WO 20080134474 A2 11/2008
(Continued)

OTHER PUBLICATIONS

Wang et al, Molecular Oncology (2014), vol. 8, pp. 1640-1652. (Year: 2014).*
(Continued)

*Primary Examiner* — Craig D Ricci
*Assistant Examiner* — Janet L. Coppins
(74) *Attorney, Agent, or Firm* — Haukaas Fortius PLLC; Michael H. Haukaas

(57) ABSTRACT

The invention provides compositions and methods for the induction of cancer cell death. The compositions and methods of using them include use of compositions in therapy for the treatment of cancer and for the selective induction of apoptosis in cancer cells. The drug combinations described herein can be synergistic and can have lower neurotoxicity effects than the same amounts of other compounds and combinations of compounds, and can be effective when a particular cancer has become resistant to previously administered therapies.

4 Claims, 26 Drawing Sheets

(51) Int. Cl.
| | |
|---|---|
| A61K 45/06 | (2006.01) |
| A61K 31/4184 | (2006.01) |
| A61K 31/437 | (2006.01) |
| A61K 31/4439 | (2006.01) |
| A61P 35/02 | (2006.01) |
| A61K 31/519 | (2006.01) |
| A61K 9/00 | (2006.01) |
| A61K 9/12 | (2006.01) |
| A61K 9/20 | (2006.01) |
| A61K 9/48 | (2006.01) |

(52) U.S. Cl.
CPC .......... *A61K 9/2027* (2013.01); *A61K 9/2054* (2013.01); *A61K 9/2059* (2013.01); *A61K 9/4866* (2013.01); *A61K 31/4184* (2013.01); *A61K 31/437* (2013.01); *A61K 31/4439* (2013.01); *A61K 31/495* (2013.01); *A61K 31/519* (2013.01); *A61K 45/06* (2013.01); *A61P 35/02* (2018.01); *A61K 2300/00* (2013.01)

(58) Field of Classification Search
USPC .................................................. 514/252.12
See application file for complete search history.

(56) References Cited

U.S. PATENT DOCUMENTS

| | | | |
|---|---|---|---|
| 8,916,705 | B2 | 12/2014 | Hergenrother |
| 9,102,661 | B2 | 8/2015 | Hergenrother et al. |
| 9,249,116 | B2 | 2/2016 | Hergenrother et al. |
| 9,399,035 | B2 | 7/2016 | Hergenrother et al. |
| 9,421,202 | B2 | 8/2016 | Hergenrother et al. |
| 9,522,901 | B2 | 12/2016 | Hergenrother et al. |
| 9,592,229 | B2 | 3/2017 | Hergenrother et al. |
| 9,643,960 | B2 | 5/2017 | Hergenrother et al. |
| 9,663,482 | B2 | 5/2017 | Hergenrother et al. |
| 2015/0017264 | A1 | 1/2015 | Hergenrother et al. |
| 2015/0231132 | A1 | 8/2015 | Hergenrother |
| 2016/0346277 | A1 | 12/2016 | Hergenrother et al. |
| 2017/0042886 | A1 | 2/2017 | Hergenrother et al. |
| 2017/0105989 | A1 | 4/2017 | Hergenrother et al. |

FOREIGN PATENT DOCUMENTS

| | | | |
|---|---|---|---|
| WO | 2010091382 A1 | 8/2010 | |
| WO | WO-2014072357 A1 * | 5/2014 | ......... A61K 31/4184 |
| WO | 2014138279 A1 | 9/2014 | |

OTHER PUBLICATIONS

Atefi et al., "Reversing Melanoma Cross-Resistance to BRAF and MEK Inhibitors by Co-Targeting the AKT/mTOR Pathway," PLoS One., 6(12):e28973, Dec. 2011.

Chen et al., "Caspases and Inhibitor of Apoptosis Proteins in Cutaneous and Mucosal Melanoma: Expression Profile and Clinicopathologic Significance," Hum Pathol., 40(7):950-956, Jul. 2009.

International Search Report and Written Opinion of the ISA/US dated Sep. 14, 2016 in International Application No. PCT/US2016/036063; 15pgs.

Joseph et al., "The RAP Inhibitor PLX4032 Inhibits ERK Signaling and Tumor Cell Proliferation in a V600E BRAF-Selective Manner," Proc Natl Acad Sci U S A., 107(33):14903-14908, Aug. 2010.

Larkin et al., "Combined Vemurafenib and Cobimetinib in BRAF-Mutated Melanoma," N Engl J Med., 371 (20):1867-1876, Nov. 2014.

Patel et al., "Expression of Executioner Procaspases and Their Activation by a Procaspase-Activating Compound in Chronic Lymphocytic Leukemia Cells," Blood, 125(7):1126-1136, Feb. 2015.

Robert et al., "Improved Overall Survival in Melanoma with Combined Dabrafenib and Trametinib," N Engl J Med, 372(1):30-39, Jan. 2015.

Sweetlove et al., "Inhibitors of Pan-PI3K Signaling Synergize with BRAF or MEK Inhibitors to Prevent BRAF-Mutant Melanoma Cell Growth," Front Oncol., 5(135):1-14, Jun. 2015.

Wang et al. "A Novel Small-Molecule Activator of Procaspase-3 Induces Apoptosis in Cancer Cells and Reduces Tumor Growth in Human Breast, Liver and Gallbladder Cancer Xenografts," Mol Oncol., 8(8):1640-1652, Dec. 2014.

Ryu et al., "Therapeutic Inhibitors against Mutated BRAF and MEK for the Treatment of Metastatic Melanoma," Chonnam Med J., 53(3):173-177, Sep. 2017.

* cited by examiner

PAC-1 COMBINATION THERAPY

RELATED APPLICATIONS

This application is a National Stage filing under 35 U.S.C. § 371 of International Application No. PCT/US2016/036063 filed Jun. 6, 2016, which claims priority under 35 U.S.C. § 119(e) to U.S. Provisional Patent Application Nos. 62/171,882, filed Jun. 5, 2015, and 62/345,629, filed Jun. 3, 2016, which applications are incorporated herein by reference.

GOVERNMENT SUPPORT

This invention was made with government support under Grant No. R01 CA120439 awarded by the National Institutes of Health. The government has certain rights in the invention.

BACKGROUND OF THE INVENTION

Apoptosis, or programmed cell death, plays a central role in the development and homeostasis of all multicellular organisms. A frequent hallmark of cancer is resistance to natural apoptotic signals. Depending on the cancer type, this resistance can be due to up- or down-regulation of key proteins in the apoptotic cascade. The resistance can also be due to mutations in genes encoding these proteins. These changes can occur in both the intrinsic apoptotic pathway, which funnels through the mitochondria and caspase-9, and the extrinsic apoptotic pathway, which involves the action of death receptors and caspase-8. For example, alterations in healthy levels of proteins such as p53, Bim, Bax, Apaf-1, FLIP and many others have been observed in cancers. These alterations can lead to a defective apoptotic cascade, one in which the upstream proapoptotic signal is not adequately transmitted to activate the executioner caspases, caspase-3 and caspase-7.

As most apoptotic pathways ultimately involve the activation of procaspase-3, upstream genetic abnormalities are effectively "breaks" in the apoptotic circuitry, and as a result such cells proliferate atypically. Given the central role of apoptosis in cancer, efforts have been made to develop therapeutics that target specific proteins in the apoptotic cascade. However, because these therapeutics target early (or intermediate to high) positions on the apoptotic cascade, cancers with mutations in proteins downstream of those members can still be resistant to the possible beneficial effects of those compounds.

For therapeutic purposes, it would be advantageous to identify small molecules that directly activate a proapoptotic protein far downstream in the apoptotic cascade. This approach could involve a relatively low position in the cascade, thus enabling the killing of even those cells that have mutations in their upstream apoptotic machinery. Moreover, such therapeutic strategies would have a higher likelihood of success if that proapoptotic protein were upregulated in cancer cells. Thus, identifying small molecules that target the downstream effector protein of apoptosis, procaspase-3, would significantly aid current cancer therapy.

The conversion or activation of procaspase-3 to caspase-3 results in generation of the active "executioner" caspase form that subsequently catalyzes the hydrolysis of a multitude of protein substrates. In certain cancers, the levels of procaspase-3 are elevated relative to normal tissue. A study of primary isolates from 20 colon cancer patients revealed that on average, procaspase-3 was upregulated six-fold in such isolates relative to adjacent non-cancerous tissue. In addition, procaspase-3 is upregulated in certain neuroblastomas, lymphomas, and liver cancers. Furthermore, a systematic evaluation of procaspase-3 levels in the 60 cell-line panel used for cancer screening by the National Cancer Institute Developmental Therapeutics Program was performed. The evaluation revealed that certain lung, melanoma, renal, and breast cancers show greatly enhanced levels of procaspase-3 expression. Due to the role of active caspase-3 in achieving apoptosis, the relatively high levels of procaspase-3 in certain cancerous cell types, and the intriguing safety catch-mediated suppression of its autoactivation, small molecules that directly modify procaspase-3, could have great applicability in targeted cancer therapy.

Furthermore, combination therapy has become increasingly important for the treatment of cancer patients. The goal of combination therapy is to achieve an additive or synergistic effect between chemotherapeutics, thereby facilitating shortened treatment times, decreased toxicity, and increased patient survival. Drugs that act on a single biochemical pathway are particularly strong candidates for synergy or potentiation as they may mimic "synthetic lethal" genetic combinations. Thus, there is an urgent a need for more effective therapies for the treatment of many forms of cancer, and new synergistic combinations of anticancer drugs would aid this pursuit. Accordingly, there exists a need to identify new combinations of cytotoxic agents that are effective in killing cancer cells, yet protect normal host tissues from the undesired toxicity of the cytotoxic agent.

SUMMARY

The invention provides compositions that include a combination of active agents for therapeutic cancer treatment. The compositions include small molecule drugs capable of inducing cancer cell death. The combination of drugs can be applicable to a variety of cancer diseases and cancer cell types such as melanoma, adrenal, brain, breast, colorectal, esophageal, gallbladder, leukemia, liver, lung, lymphoma, neuroblastoma, ovarian, pancreatic, renal, thyroid, Erdheim-Chester disease (ECD), Langerhans'-cell histiocytosis (LCH), and others known in the art. In some embodiments, the compositions interact directly or indirectly with programmed cell death pathway members such as procaspase-3. In various embodiments, the compositions are selective for a particular type of cancer cells, and can have reduced neurotoxicity compared to other compounds that interact with programmed cell death pathway members such as procaspase-3.

The combination anticancer therapy described herein can include drugs that target different biochemical pathways, or drugs that hit different targets in the same pathway, mimicking "synthetic lethal" genetic combinations. The combination of the procaspase-3 activator PAC-1 and inhibitors of the BRAF kinase that has the V600E mutation shows considerable synergy toward inducing apoptotic death of cancer cells to a degree well exceeding the additive effect. The combination of PAC-1 and these inhibitors of the BRAF gene/enzyme can effectively reduce tumor burden in tumor models in which the compounds alone have minimal or no effect. Data indicate significant efficacy for the combination of PAC-1 and these inhibitors of the BRAF enzyme for the treatment of cancer and, more broadly, show that this synergistic combination can provide significantly heightened therapeutic benefits.

Accordingly, the invention provides a composition comprising (a) the compound PAC-1:

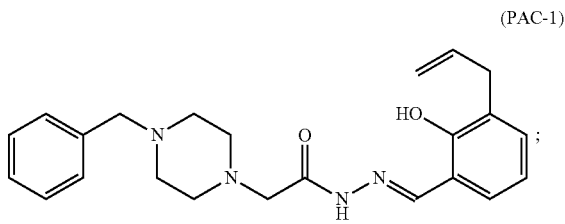 [SMILES: C=CCc1cccc(/C=N/NC(=O)CN2CCN(Cc3ccccc3)CC2)c1O]

(PAC-1)

(b) a second active agent, which agent is an inhibitor of the BRAF enzyme that has a mutation; and
(c) a pharmaceutically acceptable diluent, excipient, or carrier.

The inhibitor of the BRAF enzyme that has a mutation can be, for example, vemurafenib, dabrafenib, BMS-908662 (Bristol-Myers Squibb), encorafenib (LGX818) (Novartis), PLX3603 (RO5212054) (Hofmann-LaRoche), RAF265 (Novartis), sorafenib, or a derivative or prodrug of one of the aforementioned actives. Particularly effective inhibitors of the BRAF enzyme are inhibitors of the BRAF enzyme that has the V600E or the V600K mutation. Such inhibitors include vemurafenib and dabrafenib. In other embodiments, the composition further includes a MEK inhibitor, such as trametinib. Alternatively, the second active agent (which agent is an inhibitor of the BRAF enzyme that has a mutation) can be replaced with a MEK inhibitor such as trametinib to provide a distinct two-agent composition. In various embodiments, these actives can be administered to a patient concurrently or consecutively. A carrier for the composition can include water and/or optional components for advantageously delivering the actives such as a buffer, a sugar, a cellulose, a cyclodextrin, or various combinations thereof. In one embodiment, the cyclodextrin is 2-hydroxypropyl-β-cyclodextrin.

The invention also provides a method of inhibiting the growth or proliferation of cancer cells. This method includes contacting cancer cells with an effective amount of a composition of described herein, wherein the composition can include one or both of PAC-1 (i.e., the first active agent) and one or more second active agents (e.g., an inhibitor of the BRAF enzyme that has a mutation, and/or a MEK inhibitor). When the composition includes only one of PAC-1 and the second active agent, the method can include subsequently contacting the cancer cells with the other(s). The method can thus also include contacting cancer cells with an effective amount of a MEK inhibitor, concurrently or sequentially with PAC-1 and the second active agent. Contacting the cancer cells with these actives (e.g., PAC-1 and the second and/or third active agent) effectively inhibits the growth or proliferation of the cancer cells.

The invention further provides a method of inducing apoptosis in a cancer cell. The method can include comprising contacting the cancer cell with an effective amount of PAC-1 and an effective amount of a second and/or third active agent, wherein apoptosis is thereby induced in the cancer cell. The contacting can be in vitro. Alternatively, the contacting can be in vivo. In one embodiment, the cancer cell can be contacted with PAC-1 and the second active agent concurrently. In another embodiment, the cancer cell can be contacted with the second active agent prior to contacting the cancer cell with PAC-1. In yet another embodiment, the cancer cell can be contacted with PAC-1 prior to contacting the cancer cell with the second active agent. The third active agent (e.g., a MEK inhibitor) can be administered to the cancer cell before or after PAC-1, and before or after the second active agent.

The invention also provides a method of treating a cancer in a patient in need thereof. The method includes administering to a patient, concurrently or sequentially, a therapeutically effective amount of a compound of PAC-1, and a second active agent, which agent is an inhibitor of the BRAF enzyme that has a mutation, for example, the V600E mutation or the V600K mutation, wherein the cancer is thereby treated. In certain specific embodiments, the second active agent is vemurafenib or dabrafenib:

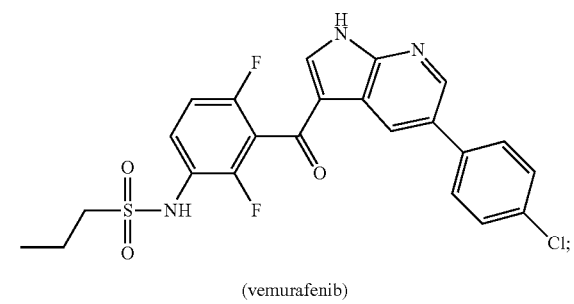

(vemurafenib)

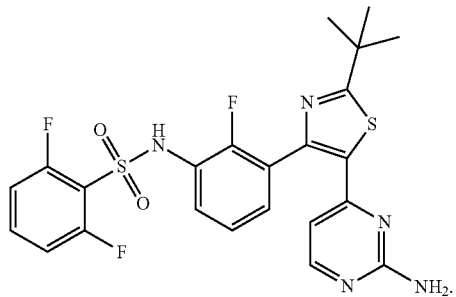

(dabrafenib)

As discussed above, PAC-1 and the second active agent can be administered concurrently. In another embodiment, PAC-1 and the second active agent are administered sequentially. When administered sequentially, the second active agent can be administered before PAC-1, or the second active agent can be administered after PAC-1. In additional embodiments, a therapeutically effective amount of a MEK inhibitor can be administered to the patient. The MEK inhibitor can be administered concurrently or sequentially with respect to PAC-1 and the second active agent. Thus, in various embodiments, the MEK inhibitor can be administered prior to, concurrently with, or after either PAC-1 or the second active agent.

The cancer (or cancer cells, as the case may be) contacted or treated can be, for example, melanoma, adrenal cancer, brain cancer, breast cancer, colorectal cancer, esophageal cancer, gallbladder cancer, liver cancer, lung cancer, lymphoma, neuroblastoma, ovarian cancer, pancreatic cancer, renal cancer, thyroid cancer, Erdheim-Chester disease (ECD), Langerhans'-cell histiocytosis (LCH), or leukemia, including hairy-cell leukemia. The melanoma can be a BRAFi-resistant melanoma, including vemurafenib-resistant melanomas. The thyroid cancer can be papillary thyroid cancer. The lung cancer can be non-small cell lung cancer (NSCLC). In some embodiments, the cancer can be brain cancer, lymphoma, or cancer cells in bone tissue. For example, the cancer can be glioblastoma or oligodendroglioma. In another embodiment, cancer cells can be osteosarcoma cells and the cancer treated is bone cancer. Other types of cancer cells that can be killed or inhibited, and other cancerous conditions that can be treated are described below.

The invention thus provides for the use of the compositions described herein for use in medical therapy. The medical therapy can be treating cancer, for example, melanoma and/or other cancers recited herein. The invention also provides for the use of a composition as described herein for the manufacture of a medicament to treat a disease in a mammal, for example, cancer in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

Figure 1A:
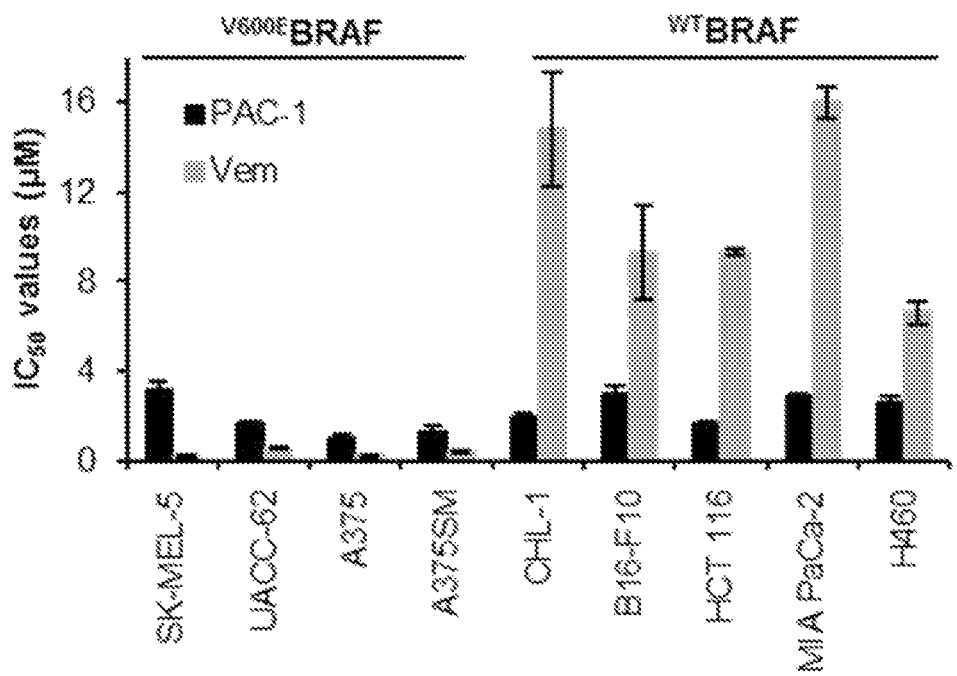
FIGS. 1A-C. The effect of vemurafenib and PAC-1 in 6 $^{V600E}$BRAF or $^{WT}$BRAF cell lines. (A) IC$_{50}$ values (5 day) of vemurafenib and PAC-1 in a panel of nine cell lines. (B) and (C): Cell lines with $^{V600E}$BRAF have significantly higher percent of cells undergoing apoptosis (assessed by Annexin V-FITC/PI staining) after treatment with vemurafenib (10 µM) and PAC-1 (12 µM) (B), or vemurafenib (0.5 µM) and PAC-1 (12 µM) (C), for 24 h, whereas this combination has negligible effect on cell lines with wild-type BRAF. Dashed horizontal lines represent the level of cell death expected from a mere additive effect of the two agents. Values are reported as mean±SEM of at least three independent experiments. P-values shown for 2-way interaction to determine if the combination for induction of apoptosis is different from an additive effect (dashed horizontal lines) of individual agents are statistically significant (* $p<0.05$,  $p<0.01$, * $p<0.001$).

FIGS. 6A-D. PAC-1 retains activity in vemurafenib-resistant A375VR cells (A) Vemurafenib is significantly less active in A375R versus parent A375. (B) Treatment with 0.5 or 1 µM of vemurafenib is unable to inhibit phosphorylation of ERK1/2 in A375VR after 2 h. Under the same conditions, complete inhibition of ERK1/2 phosphorylation was observed in the parental A375 cell line. (C) PAC-1 retains activity in the A375R cell line. Values are reported as mean±SEM of at least three independent experiments. (D) The effect of PAC-1, vemurafenib, and their combination in the A375VR xenograft model. Mice bearing subcutaneous tumors were dosed for 15 days. Mice were dosed with PAC-1 twice daily at 100 mg/kg (n=7) by i.p. injection, vemurafenib twice daily at 10 mg/kg (n=5) by (p.o.), or the PAC-1+vemurafenib combination (n=5). The black line above the x-axis indicates the dosing period for the mice during the study. Tumor volumes are plotted as mean+SEM. P-values shown are with respect to control mice. (* $p<0.05$).

FIGS. 7A-E. PAC-1 and vemurafenib powerfully synergize to induce apoptotic death and caspase activity in SK-MEL-5 cells. (A) Shown is percent apoptotic cell death (assessed by Annexin V/PI staining and flow cytometry) induced after 24 h of treatment. Values shown are heat mapped with white representing low % apoptotic cell death and dark gray representing high % apoptotic cell death. (B) Combination indices (CI) calculated for each combination with Combosyn software. CI values are heat mapped with lowest values in light gray and the highest values in black. (C) Significant caspase-3/-7 enzymatic activity is observed in cells treated with the combination of PAC-1 and vemurafenib; PAC-1 (12 µM) and vemurafenib (10 µM) alone have little effect (p-values vs. DMSO control >0.1 at all timepoints). Caspase-3/-7 activity in cell lysates was assessed with the fluorogenic Ac-DEVD-AFC substrate. Activity is expressed as normalized to minimal and maximal activity observed within the assay, with 1 µM staurosporine (STS) as the positive control. (D) PAC-1 (12 µM) and vemurafenib (10 µM) alone have little effect on PARP-1 cleavage in SK-MEL-5 cells, but significant PARP-1 cleavage is observed via western blot with the combination. (E) After 24 h, vemurafenib (0.5 µM and 1 µM) inhibited the phosphorylation of ERK1/2 with or without addition of PAC-1, indicating that effect of PAC-1 is downstream of the MAPK pathway. However, cleaved PARP-1 was only observed in cells treated with the vemurafenib/PAC-1 combination. Values are reported as mean±SEM of at least three independent experiments. P-values shown for 2-way interaction to determine if the combination is different from additive are statistically significant at indicated timepoints. (* $p<0.05$, *** $p<0.001$).

FIGS. 8A-E. PAC-1 and vemurafenib powerfully synergize to induce apoptotic death and caspase activity in UACC-62 cells. (A) Shown is percent apoptotic cell death (assessed by Annexin V/PI staining and flow cytometry) induced after 24 h of treatment. Values shown are heat mapped with white representing low % apoptotic cell death and dark gray representing high % apoptotic cell death. (B) Combination indices (CI) calculated for each combination with Combosyn software. CI values are heat mapped with lowest values in light gray and the highest values in black. (C) Significant caspase-3/-7 enzymatic activity is observed in cells treated with the combination of PAC-1 and vemurafenib PAC-1 (12 µM) and vemurafenib (10 µM) alone have little effect (p-values vs. DMSO control >0.1 at all timepoints). Caspase-3/-7 activity in cell lysates was assessed with the fluorogenic Ac-DEVD-AFC substrate. Activity is expressed as normalized to minimal and maximal activity observed within the assay, with 1 µM STS as the positive control. (D) PAC-1 (12 µM) and vemurafenib (10 µM) alone have little effect on PARP-1 cleavage in UACC-62 cells, but significant PARP-1 cleavage is observed via western blot with the combination. (E) After 24 h, vemurafenib (0.5 µM and 1 µM) inhibited the phosphorylation of ERK1/2 with or without addition of PAC-1, indicating that effect of PAC-1 is downstream of the MAPK pathway. Minimal cleaved PARP-1 was observed in PAC-1 only treated cells, which was markedly increased in cells treated with the vemurafenib/PAC-1 combination. Values are reported as mean±SEM of at least three independent experiments. P-values shown for 2-way interaction to determine if the combination is different from additive are statistically significant at indicated timepoints. (*** $p<0.001$).

FIGS. 9A-D. Effect of PAC-1a (12 µM) vs PAC-1 (12 µM) in combination with vemurafenib (30 µM) in cell lines after 24 h treatment in (A) A375, (B) SK-MEL-5 and (C) UACC-62 cell lines as assessed by Annexin V-FITC/PI plots. Percent apoptosis reported is normalized relative to DMSO control sample. Dashed horizontal lines represent the level of cell death expected from a mere additive effect of the two agents. (D) PAC-1 (12 µM) and vemurafenib (10 µM) alone have minimal effect on PARP-1 cleavage in A375 cells, but increased PARP-1 cleavage is observed with the combination. PAC-1a (12 µM) in combination with vemurafenib (10 µM) does not increase PARP-1 cleavage. Values are reported as mean±SEM of at least three independent experiments. P-values shown for 2-way interaction to determine if the combination for induction of apoptosis is different from an additive effect (dashed horizontal lines) of individual agents are statistically significant (*** $p<0.001$).

Figure 10A:
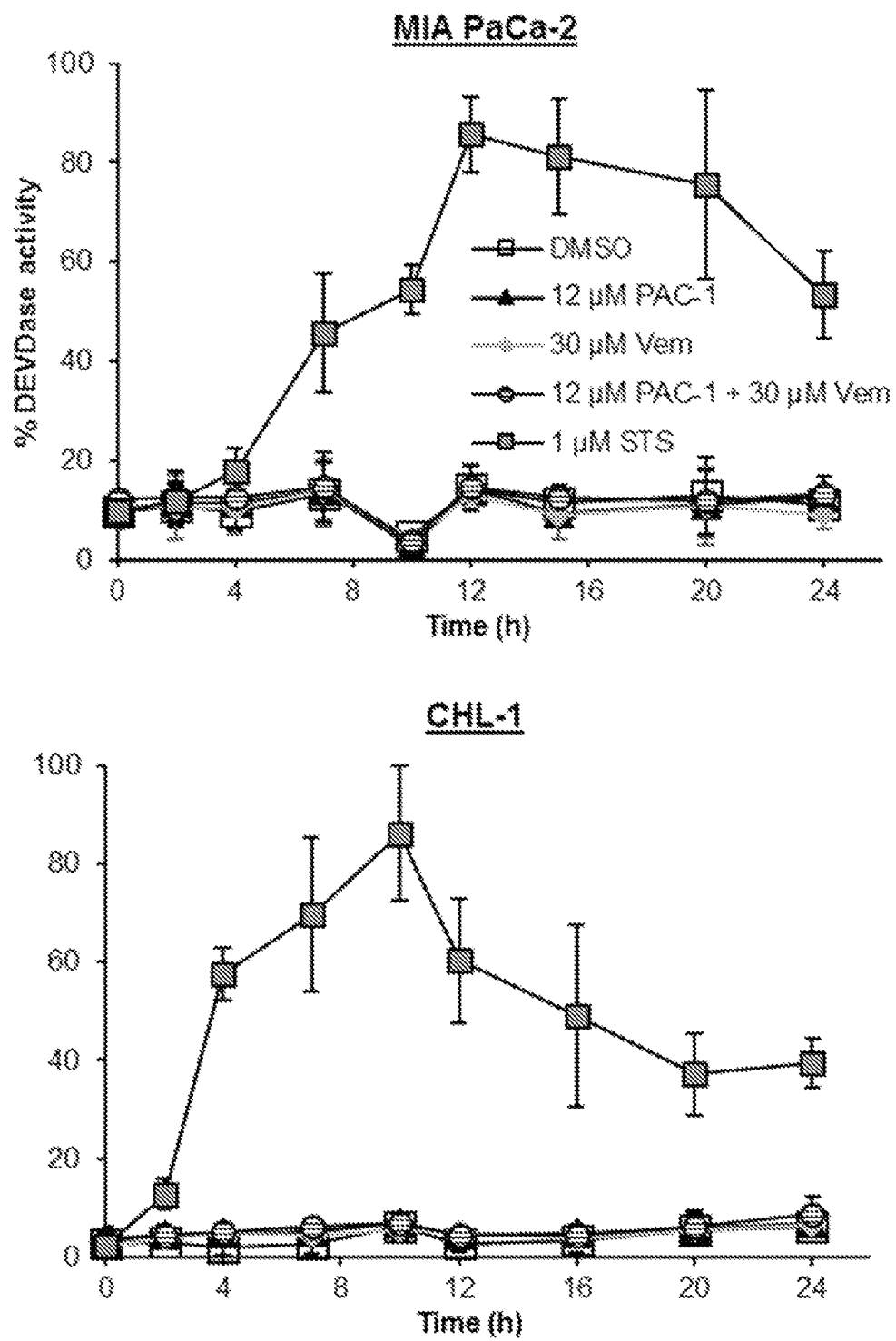
Figure 10B:
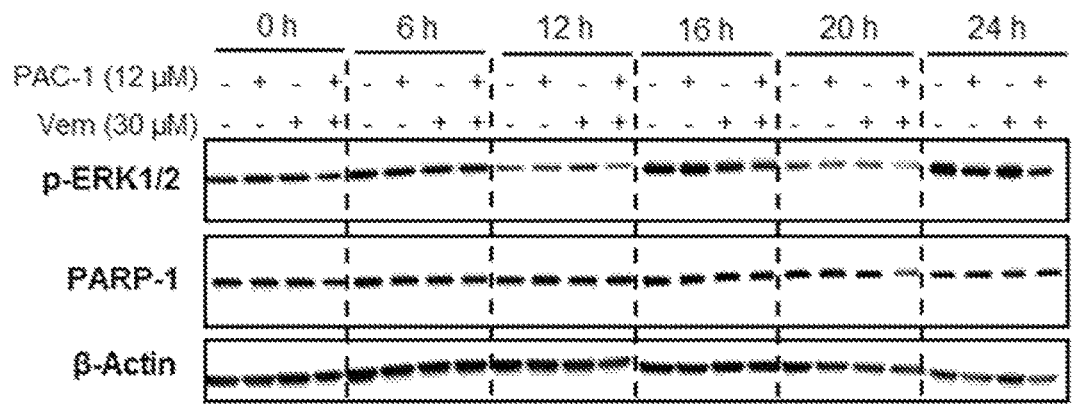
Figure 10C:
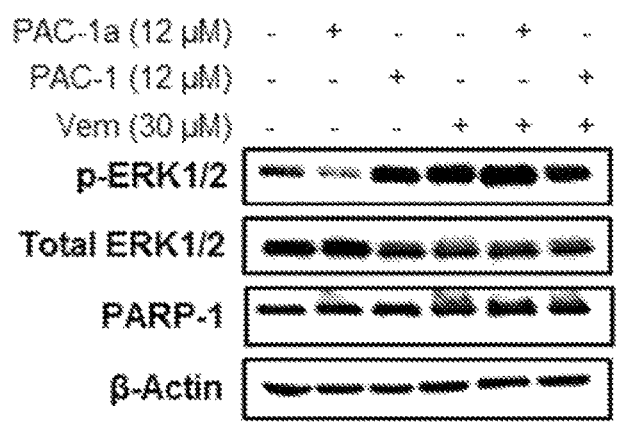

FIGS. 10A-C. Effect of the PAC-1 and vemurafenib combination in MIA PaCa-2 (mutant KRAS and $^{WT}$BRAF) and CHL-1 ($^{WT}$KRAS and $^{WT}$BRAF) cell lines with $^{WT}$BRAF. (A) No effect on procaspase-3 activation is observed in MIA PaCa-2 and CHL-1 cell lines when treated with PAC-1 (12 µM)+vemurafenib (30 Caspase-3/-7 activity in cell lysates was assessed with the fluorogenic Ac-DEVD-AFC substrate. Activity is expressed as normalized to minimal and maximal activity observed within the assay, with 1 µM STS as the positive control. (B) No effect on PARP-1 cleavage was observed in MIA PaCa-2 cells after 24 h. (C) PAC-1 (12 µM) and vemurafenib (30 µM) have no effect on PARP-1 cleavage in CHL-1 cells after 24 h treatment. Values are reported as mean±SEM of at least three independent experiments.

Figure 11:
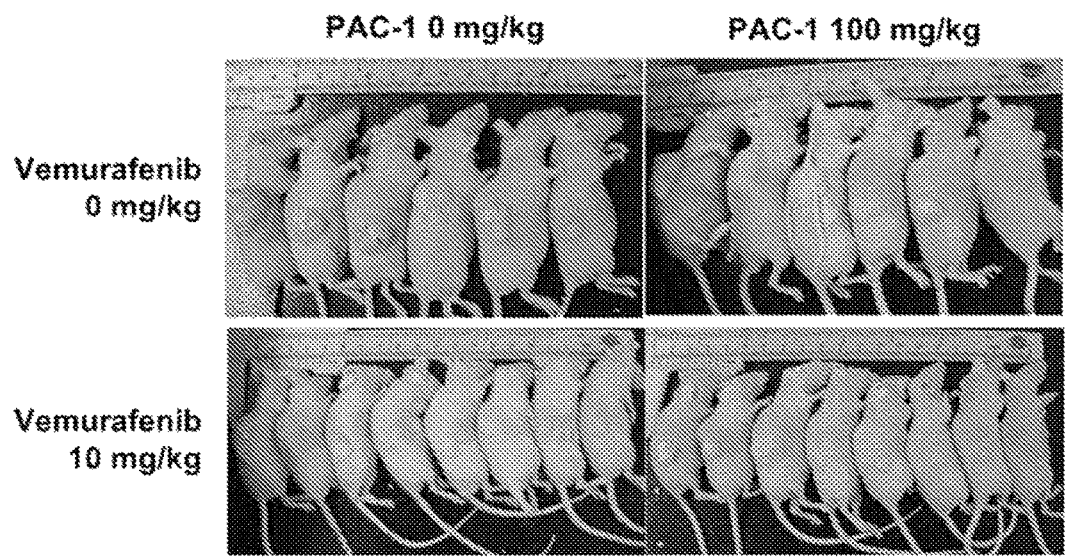

FIG. 11. Images of tumor-bearing mice that were sacrificed after 15 days of continuous dosing. The four treatment groups are: control (n=6, 0 mg/kg PAC-1 and vemurafenib); mice treated once-a-day with 100 mg/kg PAC-1 (n=6), twice-a-day with 10 mg/kg vemurafenib (n=8), and the combination of 100 mg/kg PAC-1 (once-a-day) and 10 mg/kg vemurafenib (twice-a-day) (n=8).

Figure 12A:
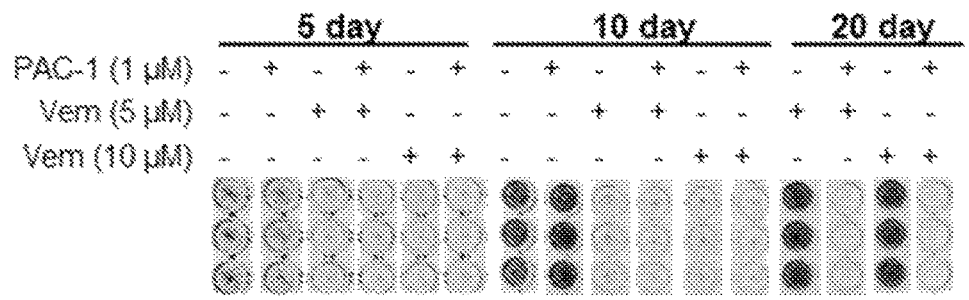
Figure 12B:
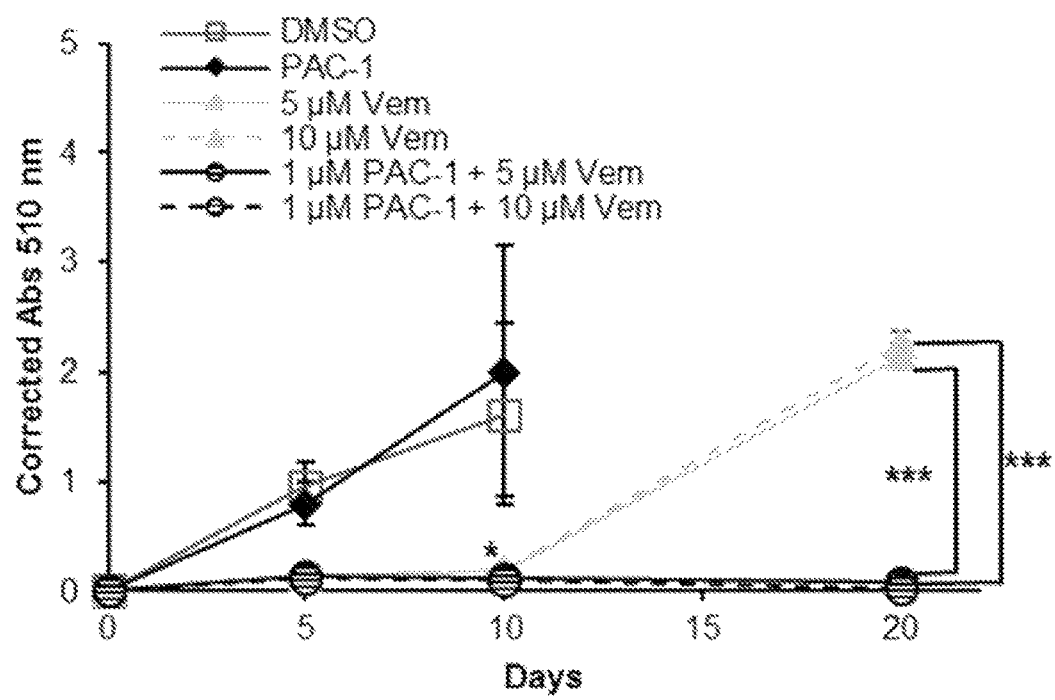

FIGS. 12A-B. Addition of PAC-1 (1 µM) in the long-term treatment of UACC-62 cells with vemurafenib significantly delays cell regrowth. (A) UACC-62 cells were treated with PAC-1 (1 µM), vemurafenib (5 µM or 10 µM), or the combination. Media was washed out every 2-3 days and new compounds were added into each well. After 5, 10 or 20 days, the wells were fixed with 10% trichloroacetic acid, stained with 0.5% sulforhodamine B (SRB) dye, and imaged with BioRad GelDoc RX. Day 20 images of control and PAC-1 samples are not shown because the cells were unviable due to overcrowding. (B) Quantification of (A) where the SRB dye is dissolved in 10 mM Tris base at pH 10.4, and the absorbance read at 510 nm. Corrected absorbance at 510 nm was plotted against the days of continuous treatment by normalizing against absorbance on Day 0 before the start of treatment. Values are reported as mean±SEM of at least three independent experiments. 2-tailed t-test performed between wells treated with vemurafenib only versus vemurafenib and PAC-1 (1 µM). On day 10, only the wells treated with vemurafenib (10 µM) and PAC-1 (1 µM) is significantly different from vemurafenib (10 µM) only (p=0.035) treatment. On day 20, wells treated with vemurafenib (5 or 10 µM) and PAC-1 (1 µM) are significantly different from vemurafenib (5 or 10 µM), as indicated on the graph. (* $p<0.05$, *** $p<0.001$).

Figures 13A, 13B, 13C:
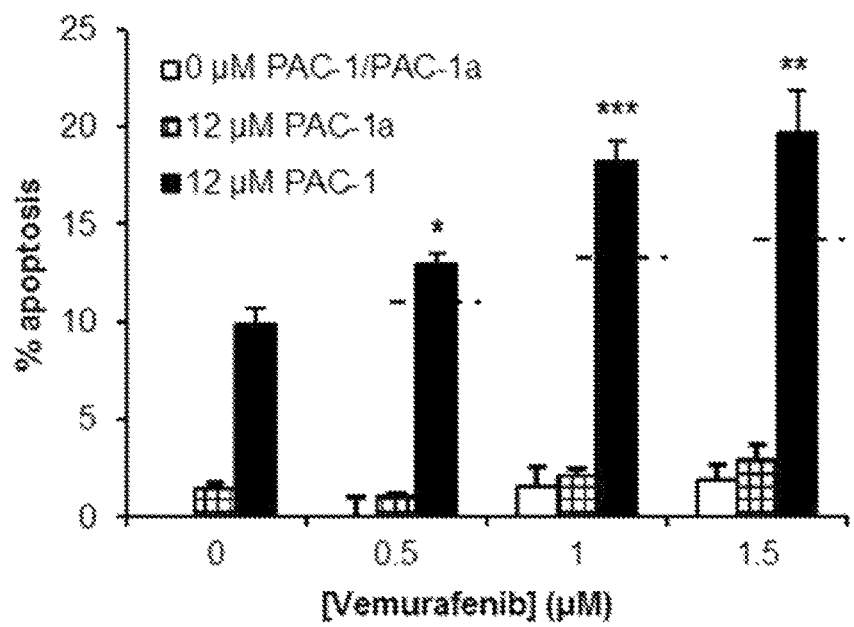

FIGS. 13A-C. Effect of the PAC-1 and vemurafenib combination in A375VR cells. (A) Shown is percent apoptotic cell death (assessed by Annexin V/PI staining and flow cytometry) induced after 24 h of treatment. (B) The apoptotic cell death observed in (A) is greater than that predicted by the Bliss independent model. The excess cell death is calculated as $[f_{(observed,\ apoptotic)} - (f_{(PAC-1,\ apoptotic)} + f_{(vemurafenib,\ apoptotic)} - f_{(PAC-1,\ apoptotic)} * f_{(vemurafenib,\ apoptotic)})] * 100\%$. This indicates that the observed effect is synergistic rather than additive. (C) The synergistic effect of PAC-1 and vemurafenib in activating apoptosis in A375VR after 24 h. This effect is abolished when the inactive PAC-1a was used. Dashed horizontal lines represent the level of cell death expected from a mere additive effect of the two agents. Values are reported as mean±SEM of at least three independent experiments. P-values shown for 2-way interaction to determine if the combination for induction of apoptosis is different from an additive effect (dashed horizontal lines) of individual agents are statistically significant (* $p<0.05$,  $p<0.01$, * $p<0.001$).

DETAILED DESCRIPTION

Many cancers resist standard chemotherapy, or become resistant to a particular chemotherapeutic after a period of time. The combination therapy described herein takes advantage of the procaspase-1 activation by PAC-1, which can synergize with the chemotherapeutic properties of a second active agent such as an inhibitor of the BRAF enzyme that has a mutation, to provide efficacy under conditions where one of the actives alone might be less effective or completely ineffective. These compounds can also be successful in targeted cancer therapy, where there can be advantages of selectivity in the killing of cancer cells with comparably reduced adverse reactions to non-cancerous cells having lower levels of procaspase-3. These reduced adverse reactions can include reductions in toxicity, particularly neurotoxicity.

The combination of compounds, the compositions and the methods described herein can act via modulation of apoptosis or programmed cell death and other chemotherapeutic mechanisms to be effective in the treatment of cancer. In one embodiment, the modulation of apoptosis is by induction or activation of apoptosis. In various embodiments, the administration of compounds can be concurrent, or alternatively, sequential.

The invention thus provides methods for potentiation of an active agent by PAC-1, for example, for the treatment of melanoma, colorectal cancer, thyroid cancer, lung cancer, or ovarian cancer. During apoptosis, the zymogen procaspase-3 is activated via proteolysis to caspase-3, and this active caspase-3 then cleaves scores of cellular substrates, executing the apoptotic program. Because procaspase-3 protein levels are elevated in various tumor histologies, drug-mediated direct activation of procaspase-3 can be highly effective as a selective anticancer strategy.

Certain compounds can enhance the activity and automaturation of procaspase-3 and induce apoptosis in cancer cells. Procaspase-activating compound-1 (PAC-1) enhances the activity of procaspase-3 via the chelation of inhibitory zinc ions, induces apoptosis in cancer cells in culture, and has efficacy in multiple murine tumor models. Novel combinations of PAC-1 and inhibitors of the BRAF enzyme that has a mutation have been found to be synergistically effective in treating cancer cells, as described herein. Because PAC-1 acts late in the apoptotic cascade, it is uniquely capable of synergizing with a wide range of chemotherapeutic active agents, as described herein.

Melanoma is the most common cutaneous malignancy and upon metastasis is considered the deadliest form of skin cancer. It is the fifth most common cancer in the United States. One common mutation in melanoma is the substitution of a valine for glutamate (V600E) in the kinase domain of the BRAF protein (Davies et al., Nature 2002, 417, 949). The V600E mutation constitutively activates BRAF and the downstream MEK-ERK signaling pathway, leading to tumorigenesis. The discovery that approximately 50% of melanomas harbor the V600E mutation in the BRAF protein spurred the development of $^{V600E}$BRAF inhibitors, and the subsequent approval of vemurafenib in 2011. $^{V600E}$BRAF inhibitors like vemurafenib (and dabrafenib, approved in 2013) lead to impressive reduction in tumor burden within weeks of therapy, and extension of progression-free survival by three to four months.

Despite their initial anti-melanoma activity, resistance to $^{V600E}$BRAF inhibitors rapidly emerges. In the majority of resistant tumors, reactivation of the MAPK signaling pathway is observed, motivating the addition of MEK1/2 inhibitors (e.g., trametinib) to the treatment regimen for metastatic melanoma. Upfront combination therapy with MEK1/2 and $^{V600E}$BRAF inhibitors is effective in delaying the median time to resistance by 3.7 to 4.1 months in patients who have not received prior $^{V600E}$BRAF inhibition treatment, but the addition of MEK1/2 inhibitor to patients who have already failed prior $^{V600E}$BRAF inhibitor therapy only results in a marginal improvement in anticancer efficacy. Given the current clinical limitations of existing therapies, novel and rationally-designed combination studies with other kinase inhibitors are being explored. Despite all efforts to date, the development of resistance to targeted $^{V600E}$BRAF therapies emerges in virtually 100% of patients treated; acquired drug resistance to this class of agents remains a significant obstacle to dramatically enhanced survival benefits for metastatic melanoma patients.

In contrast to many studies that have focused on the combination of vemurafenib with inhibitors of diverse and druggable kinases, combination therapy of vemurafenib with agents that activate the apoptotic pathway have not been extensively explored. In part, this lack of exploration might be attributed to the fact that melanoma cells possess multiple defects in their apoptotic signaling pathways, rendering them resistant to many proapoptotic stimuli. We hypothesized that a suitable proapoptotic agent that induces apoptosis downstream of these apoptotic defects would be highly synergistic with $^{V600E}$BRAF inhibitors.

Given that the aberrations in the apoptotic signaling cascades in melanoma cells are upstream of the activation of procaspase-3, drugs that directly activate procaspase-3 are intriguing candidates for this combination therapy. In addition, because melanomas have elevated expression of procaspase-3, a procaspase-3 activator should be potent and selective for such cells. Furthermore, it is known that $^{V600E}$BRAF inhibitors induce apoptotic cell death mediated by caspase-3; thus, the combination of vemurafenib with a direct procaspase-3 activator could lead to dramatically enhanced caspase-3 activity and cancer cell death relative to the effect of either single-agent. PAC-1 is a small molecule that directly activates cellular procaspase-3 via chelation of labile inhibitory zinc. Due to the overexpression of procaspase-3 in cancers of diverse origins, PAC-1 and its derivatives selectively induce apoptosis in cancer cells while sparing non-cancerous cells. PAC-1 exerts single agent activity in multiple murine models of cancer, including a xenograft model of melanoma. Importantly, in addition to favorable preclinical activity in murine tumor models, human cancer patients have been taking PAC-1 as part of a Phase I clinical trial since March 2015 (NCT02355535).

Vemurafenib, the first approved BRAF inhibitor, is a targeted therapy for melanoma patients who have the V600E BRAF protein (Bollag et al., *Nat. Rev. Drug Discov.* 2012, 11, 873). Treatment with vemurafenib leads to apoptosis and rapid tumor regression, extending the progression-free survival of melanoma patients with the V600E BRAF protein by 5.3 months (McArthur et al., *Lancet Oncol.* 2014, 15, 323). While vemurafenib represents a significant advance in the treatment of melanoma, onset of resistance has been a significant concern in the clinic. Combination therapy of vemurafenib with an MEK inhibitor has been clinically tested to extend the duration of progression-free survival by 3.7 months, but resistance ultimately arises due to reactivation of the RAF-MEK-ERK pathway (Larkin et al., *N. Engl. J. Med.* 2014, 371, 1867).

Elevated expression of procaspase-3, the executioner caspase in the apoptotic cascade, has been reported in various cancers including melanoma (Fink et al., *Melanoma Res.* 2001, 11, 385; Chen et al., *Hum. Pathol.* 2009, 40, 950). Small molecule activation of procaspase-3 is therefore an attractive therapeutic strategy for melanoma due to the key role played by procaspase-3 in the apoptotic cascade. Procaspase-3 activating compound 1 (PAC-1) is a small molecule that chelates the labile pool of zinc ions, which inhibit procapase-3, thus priming cancer cells for apoptotic death (Peterson et al., *J. Mol. Biol.* 2009, 388, 144). PAC-1 has shown single agent efficacy in a murine xenograft model of melanoma, validating the potential of procaspase-3 activation as an anti-cancer strategy (Wang et al., *Mol. Oncol.* 2014, 8, 1640). Given that PAC-1 primes cells for apoptotic death and vemurafenib induces apoptosis in cancer cells, we find that vemurafenib in combination with PAC-1 dramatically enhances therapeutic efficacy.

We recently discovered that PAC-1 shows outstanding synergy with inhibitors of the BRAF enzyme that has the V600E mutation, including vemurafenib (marketed as zelboraf), a drug that was recently approved for the treatment of melanoma. Based on our data (see FIGS. 1-13), PAC-1 will show equivalent synergy with all drugs in this class (inhibitors of the BRAF enzyme that has the V600E or the V600K mutation), which also includes dabrafenib (trade name tafinlar) and others.

The synergistic activity of inhibitors of the BRAF enzyme that has the V600E mutation, such as vemurafenib, with PAC-1 in enhancing apoptotic cell death in a variety of melanoma cell lines containing the V600E BRAF protein is described herein. Importantly, PAC-1 retains activity in vemurafenib-resistant A375R cell line, indicating its utility in melanomas that have progressed beyond BRAF-inhibitor treatment.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

"Concurrently" means (1) simultaneously in time, or (2) at different times during the course of a common treatment schedule.

"Sequentially" refers to the administration of one active agent used in the method followed by administration of another active agent. After administration of one active agent, the next active agent can be administered substantially immediately after the first, or the next active agent can be administered after an effective time period after the first active agent; the effective time period is the amount of time given for realization of maximum benefit from the administration of the first active agent.

An "effective amount" refers to an amount effective to treat a disease, disorder, and/or condition, or to bring about a recited effect, such as activation or inhibition. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat a disease or disorder, or to treat the symptoms of the disease or disorder, in a host. Thus, an "effective amount" generally means an amount that provides the desired effect.

In one embodiment, an effective amount refers to an amount of the active agent described herein that are effective, either alone or in combination with a pharmaceutical carrier, upon single- or multiple-dose administration to a cell or a subject, e.g., a patient, at inhibiting the growth or proliferation, inducing the killing, or halting the growth of hyperproliferative cells. Such growth inhibition or killing can be reflected as a prolongation of the survival of the subject, e.g., a patient beyond that expected in the absence of such treatment, or any improvement in the prognosis of the subject relative to the absence of such treatment.

The terms "treating", "treat" and "treatment" include (i) inhibiting the disease, pathologic or medical condition or arresting its development; (ii) relieving the disease, pathologic or medical condition; and/or (iii) diminishing symptoms associated with the disease, pathologic or medical condition. Thus, the terms "treat", "treatment", and "treating" can include lowering, stopping or reversing the progression or severity of the condition or symptoms being treated. As such, the term "treatment" can include medical and/or therapeutic administration, as appropriate. In some embodiments, the terms "treatment", "treat" or "treated" can refer to (i) a reduction or elimination of symptoms or the disease of interest (therapy) or (ii) the elimination or destruction of the tumor (cure).

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting. Additionally, the terms "induce," "inhibit," "potentiate," "elevate," "increase," "decrease," or the like denote quantitative differences between two states, and can refer to at least statistically significant differences between the two states. For example, "an amount effective to inhibit the growth of hyperproliferative cells" means that the rate of growth of the cells can be, in some embodiments, at least statistically significantly different from the untreated cells. Such terms can be applied herein to, for example, rates of proliferation.

The phrase "inhibiting the growth or proliferation" of the hyperproliferative cell, e.g. neoplastic cell, refers to the slowing, interrupting, arresting, or stopping its growth and metastasis, and does not necessarily indicate a total elimination of the neoplastic growth.

The term "cancer" generally refers to any of a group of more than 100 diseases caused by the uncontrolled growth of abnormal cells. Cancer can take the form of solid tumors and lymphomas, and non-solid cancers such as leukemia. Unlike normal cells, which reproduce until maturation and then only as necessary to replace wounded cells, cancer cells can grow and divide endlessly, crowding out nearby cells and eventually spreading to other parts of the body.

The invention provides methods for treating cancer and cancerous conditions, and particularly cancers that carry the V600E BRAF protein or the V600K BRAF protein. The term "cancerous condition" relates to any condition where cells are in an abnormal state or condition that is characterized by rapid proliferation or neoplasia. A cancerous condition may be malignant or non-malignant (e.g. precancerous condition) in nature. To farther describe a "cancerous condition", the terms "hyperproliferative", "hyperplastic", "hyperplasia", "malignant", "neoplastic" and "neoplasia" can be used. These terms can be used interchangeably and are meant to include all types of hyperproliferative growth, hyperplastic growth, cancerous growths or oncogenic processes, metastatic tissues or malignantly transformed cells, tissues or organs, irrespective of histopathologic type, stage of invasiveness, or cancerous determination (e.g. malignant and nonmalignant).

The term "neoplasia" refers to new cell growth that results in a loss of responsiveness to normal growth controls, e.g., neoplastic cell growth. A "hyperplasia" refers to cells undergoing an abnormally high rate of growth. However, these terms can be used interchangeably, as their context will reveal, referring generally to cells experiencing abnormal cell growth rates. "Neoplasias" and "hyperplasias" include tumors, which may be either benign, premalignant, carcinoma in-situ, malignant, solid or non-solid. Examples of some cancerous conditions that are can be treated include, but are not limited to, anal cancer, transitional cell bladder cancer, bone cancer, breast cancer, cervical cancer, colorectal cancer, gastric cancer, head and neck cancer, Kaposi's sarcoma, leukemia, lung cancer such as bronchogenic lung cancer, small cell lung cancer, and non-small cell lung cancer, Hodgkin's lymphoma, Non-Hodgkin's lymphoma, malignant lymphoma, neuroblastomas, osteogenic carcinomas (e.g. cancer of the bone), ophthalmic cancers (e.g. retinoblastomas and other cancers of the eye), ovarian cancer, prostate cancer, renal cancer, skin cancers such as melanoma, soft tissue sarcomas, thyroid cancer, and Wilms' tumor. Other examples of non-malignant hyperproliferative conditions (e.g. precancerous conditions) that are within the scope of the invention include, but are not limited to, adenomas, chondromas, enchondromas, fibromas, myomas, myxomas, neurinomas, osteoblastomas, osteochondromas, osteomas, papillary tumors, and the like, including other cancers described herein.

The terms "leukemia" or "leukemic cancer" refer to all cancers or neoplasias of the hematopoetic and immune systems (blood and lymphatic system). These terms refer to a progressive, malignant disease of the blood-forming organs, marked by distorted proliferation and development of leukocytes and their precursors in the blood and bone marrow. Myelomas refer to other types of tumors of the blood and bone marrow cells. Lymphomas refer to tumors of the lymph tissue. Examples of leukemia include acute myelogenous leukemia (AML), acute lymphoblastic leukemia (ALL), and chronic myelogenous leukemia (CIVIL).

As described herein, the compositions and methods of the invention can be used for the treatment of various neoplasia disorders including such conditions as acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor. Accordingly, the compositions and methods described herein can be used to treat skin cancer, bladder cancer, brain cancer (including intracranial neoplasms such as glioma, meninigioma, neurinoma, and adenoma), breast cancer, colon cancer, lung cancer (SCLC or NSCLC), ovarian cancer, pancreatic cancer, prostate cancer, and/or other cancers recited herein.

In some embodiments, the combination of PAC-1 and a second active agent (e.g., an inhibitor of the BRAF enzyme that has a mutation, for example, the active agent vemurafenib) can be particularly effective for treating melanoma. Other cancers that can be treated include, but are not limited to, oligodendrogliomas and glioblastomas including glioblastoma multiforme (GBM). Tissues affected by the cancerous cells can be in the brain itself (e.g., the cranium or the central spinal canal) or in lymphatic tissue, in blood vessels, in the cranial nerves, in the brain envelopes (meninges), skull, pituitary gland, or pineal gland. Specific forms of brain cancer that can be treated include astrocytomas, chondromas, chondrosarcomas, chordomas, CNS (central nervous system) lymphomas, craniopharyngiomas, ependymomas, gangliogliomas, ganglioneuromas (also called gangliocytomas), gliomas, including astrocytomas, oligodendrogliomas, and ependymomas, hemangioblastomas (also called vascular tumors), primitive neuroectodermal tumors (PNET) such as medulloblastomas, meningiomas, and vestibular schwannomas (formerly known as acoustic neuroma/schwannoma).

The combination can also be used to treat metastatic tumors that invade the intracranial sphere from cancers originating in other organs of the body. These conditions are typically referred to as secondary brain tumors. Secondary brain tumors that can be treated with the combination of PAC-1 and a second active agent include metastatic tumors of the brain that originate from lung cancer, breast cancer, malignant melanoma, kidney cancer, colon cancer, and other carcinomas.

Other examples of cancerous conditions that are within the scope of the invention include, but are not limited to, neuroblastomas and osteogenic carcinomas (e.g. cancer of the bone or neoplastic growth of tissue in bone). Examples of malignant primary bone tumors that can be treated with the combination of PAC-1 and a second active agent include osteosarcomas, chondrosarcomas, Ewing's sarcoma, fibrosarcomas, and the like, and secondary bone tumors such as metastatic lesions that have spread from other organs, including carcinomas of the breast, lung, and prostate.

Therapeutic Agents and Activity

Procaspase-activating compound-1 (PAC-1; (2-(4-benzylpiperazin-1-yl)-N-[(2-hydroxy-3-prop-2-enyl-phenyl) methylideneamino]acetamide) selectively induces apoptosis in cancerous cells. Methods of preparing PAC-1 are described in U.S. Pat. No. 8,778,945 (Hergenrother et al.). PAC-1 enhances the activity of procaspase-3 via the chelation of inhibitory zinc ions, induces apoptosis in cancer cells. PAC-1 can enhance the activity and automaturation of procaspase-3 and induce apoptosis in cancer cells. PAC-1 also enhances the chemotherapeutic activity of inhibitors of the BRAF enzyme having a mutation (the second active), often where either PAC-1 or the second active is less effective or completely inactive alone.

It was surprisingly discovered that PAC-1 and its derivatives can synergize the activity of inhibitors of the BRAF enzyme having a mutation. Accordingly, the invention provides further embodiments where the active agent PAC-1 in the compositions described herein can be exchanged for a PAC-1 derivative as described in U.S. Pat. No. 8,592,584 (Hergenrother et al.) or U.S. Pat. No. 8,778,945 (Hergenrother et al.), which patents are incorporated herein by reference, to provide additional compositions of the invention. One example of such PAC-1 derivatives is SPAC-1 (4-((4-(2-(2-(3-allyl-2-hydroxybenzylidene)hydrazinyl)-2-oxoethyl)piperazin-1-yl)methyl)benzenesulfonamide).

PAC-1 and its derivatives can also synergize the activity of MEK inhibitors such as trametinib.

Accordingly, PAC-1 can be combined with an inhibitor of the BRAF enzyme that has a mutation, as described herein, and/or with an MEK inhibitor such as trametinib, cobimetinib, binimetinib (MEK162), selumetinib, PD-325901, CI-1040, PD035901, or TAK-733. MEK inhibitors are drugs that inhibit the mitogen-activated protein kinase kinase enzymes MEK1 and/or MEK2. They can be used to affect the MAPK/ERK pathway, which is overactive in certain cancers.

The amount or concentration of PAC-1 or the PAC-1 derivative in a therapeutic composition can be the amount or concentration effective to inhibit cancer cell growth, to induce apoptosis in a cancer cell, or to synergize with the second active agent. For example, the concentration of PAC-1 can be about 0.2 µM to about 5 mM, or about 2 µM to about 50 µM, typically about 2.5 µM, about 5 µM, about 7.5 µM, about 10 µM, about 12.5 µM, about 15 µM, about 20 µM, about 25 µM, about 30 µM, about 40 µM, or about 50 µM, or a range between any of the aforementioned values. Similarly, the concentration of the second active agent (e.g., inhibitors of the BRAF enzyme having a mutation such as vemurafenib or dabrafenib) can be about 1 nM to about 1 mM, or about 25 nM to about 1 mM, typically about 1 nM, about 2 nM, about 3 nM, about 5 nM, about 10 nM, about 25 nM, about 50 nM, about 100 nM, about 250 nM, about 500 nM, about 750 nM, about 900 nM, about 1 µM, about 2.5 µM, about 5 µM, about 7.5 µM, about 10 µM, about 12.5 µM, about 15 µM, about 20 µM, about 25 µM, about 30 µM, about 40 µM, about 50 µM, about 75 µM, about 100 µM, about 125 µM, about 150 µM, about 200 µM, about 250 µM, about 300 µM, about 500 µM, about 750 µM, or about 1 mM, or a range between any of the aforementioned values. One of skill in the art can readily convert the amount of active agent in a dose of a particular concentration to an amount of active agent, for example, for use in a solid dosage unit.

Data for various experiments are shown in FIGS. 1-13. PAC-1 and vemurafenib powerfully synergize to induce apoptotic death and caspase activity in melanoma cells. A dramatic procaspase-3 activation is observed in cells treated with PAC-1+vemurafenib. Additionally, 12 µM PAC-1 and 10 µM vemurafenib alone have little effect on PARP-1 cleavage in A375 cells, but significant PARP cleavage is observed (via western blot) with the combination. Furthermore, the addition of PAC-1 to the combination of vemurafenib and an MEK inhibitor, trametinib, significantly enhances the caspase-3 activity and proapoptotic effect of the combination. Moreover, addition of low concentrations of PAC-1 delays the regrowth of cancer cells following treatment with vemurafenib. PAC-1 also remains potent against vemurafenib-resistant A375VR cells in cell culture and synergizes with vemurafenib to exert antitumor effects on A375VR cell growth in vivo. Our data indicate that inhibition of MAPK signaling combined with concurrent procaspase-3 activation is an effective strategy to enhance the antitumor activity of vemurafenib and mitigate the development of resistance. Accordingly, the invention provides a method of overcoming vemurafenib resistance by administering PAC-1 in combination with vemurafenib therapy, and/or vemurafenib/MEK inhibitor therapy to patients having vemurafenib resistant cancer.

Methods of the Invention

The invention provides methods of selectively inducing apoptosis in a cancer cell, comprising administering to a cancer cell a combination of compounds capable of modifying a procaspase-3 molecule of said cancer cell; wherein the combination of compounds is PAC-1 and a second active agent. Also provided is a method of selectively inducing apoptosis in a cancer cell, comprising administering to a cancer cell a combination of compounds capable of modifying a procaspase-3 molecule of the cancer cell; wherein the combination of compounds is PAC-1 and a second active agent, for example, wherein the cancer cell is in a patient in need of treatment.

The invention provides additional methods where the recited combination of compounds is PAC-1 and a second active agent, for example, as a method of treating a cancer cell, comprising (a) identifying a potential susceptibility to treatment of a cancer cell with a procaspase activator compound; and (b) exposing the cancer cell to an effective amount of a combination of a procaspase activator compound and a second active agent. Also provided is a method of treating a cancer cell, comprising (a) identifying a potential susceptibility to treatment of a cancer cell with a procaspase activator compound; and (b) exposing said cancer cell to an effective amount of PAC-1 and a second active agent; wherein the PAC-1 is capable of activating at least one of procaspase-3 and procaspase-7. Also provided is a method of inducing death in a cancer cell (e.g., killing a cancer cell), comprising administering to a cancer cell an active agent and a compound capable of activating a procaspase-3 molecule of the cancer cell, such as PAC-1.

The invention further provides a medicament comprising an effective amount of the combination of PAC-1 and a second active agent. The medicament can be used in a method of inducing apoptosis in a cell. In some embodiments, the combination of compounds does not cross the blood-brain barrier to as extent that causes appreciable neurotoxic effects in a patient. Methods of the invention include contacting one or more cells with an effective amount of a combination of compounds described herein, in vivo or in vitro. The invention thus also provides methods of treating a cell that include contacting a cell with an effective amount of a combination of compounds described herein, and treating a patient in need of cancer therapy with an effective amount of a combination of compounds described herein.

As described herein, the invention provides methods of treating a patient that has tumor cells having elevated procaspase-3 levels. The methods can include administering to a patient having tumor cells with elevated procaspase-3 levels a therapeutically effective amount of a combination of PAC-1 and a second active agent described herein, or a composition thereof. The invention further provides methods of treating a tumor cell having an elevated procaspase-3 level comprising exposing the tumor cell to a therapeutically effective amount of a combination of PAC-1 and a second active agent described herein, wherein the tumor cell is treated, killed, or inhibited from growing. The tumor or tumor cells can be malignant tumor cells. In some embodiments, the tumor cells are melanoma, colorectal, thyroid, lung, or ovarian cancer cells.

PAC-1 can be combined with a second active agent in a unitary dosage form for the administration to a patient. The combination therapy may be administered as a simultaneous or sequential regimen. When administered sequentially, the combination may be administered in two or more administrations.

The combination therapy may provide "synergy", i.e. the effect achieved when the active ingredients used together is greater than the sum of the effects that results from using the compounds separately. A synergistic effect may be attained when PAC-1 and a second active agent are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient can be administered sequentially, i.e. serially, whereas in combination therapy, effective dosages of two or more active ingredients are administered together. A synergistic anti-cancer effect denotes an anti-cancer effect that is greater than the predicted purely additive effects of the individual compounds of the combination. Combination therapy is further described by U.S. Pat. No. 6,833,373 (McKearn et al.), which includes additional active agents that can be combined with PAC-1, and additional types of cancer and other conditions that can be treated with PAC-1.

Accordingly, PAC-1 can be used in combination with the second active agent for cancer treatment. PAC-1 may precede or follow the second active agent administration by intervals ranging from minutes to weeks. In embodiments where the second active agent and PAC-1 are applied separately to the cell, one would generally ensure that a significant period of time did not elapse between each delivery, such that the agent and PAC-1 would still be able to exert an advantageously combined effect on the cell. For example, in such instances, it is contemplated that one may contact the cell, tissue or organism with the two modalities substantially simultaneously (i.e., within less than about a few minutes). In other aspects, the second active agent of the combination may be administered within about 1 minute, about 5 minutes, about 10 minutes, about 20 minutes about 30 minutes, about 45 minutes, about 60 minutes, about 2 hours, about 3 hours, about 4 hours, about 6 hours, about 8 hours, about 9 hours, about 12 hours, about 15 hours, about 18 hours, about 21 hours, about 24 hours, about 28 hours, about 31 hours, about 35 hours, about 38 hours, about 42 hours, about 45 hours, or at about 48 hours or more, prior to and/or after administering PAC-1. In certain other embodiments, the second active agent may be administered within about 1 day, about 2 days, about 3 days, about 4 days, about 5 days, about 6 days, about 8 days, about 9 days, about 12 days, about 15 days, about 16 days, about 18 days, about 20 days, or about 21 days, prior to and/or after administering PAC-1. In some situations, it may be desirable to extend the time period for treatment significantly, however, where several weeks (e.g., about 1, about 2, about 3, about 4, about 6, or about 8 weeks or more) lapse between the respective administrations.

Administration of the chemotherapeutic compositions of the invention to a patient will typically follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described combinations. These therapies include but are not limited to chemotherapy, immunotherapy, gene therapy and surgery.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer. Thickeners such as synthetic polymers, fatty acids, fatty acid salts and esters, fatty alcohols, modified celluloses, or modified mineral materials can also be employed with liquid carriers.

Useful dosages of the active agents described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose of active agents will be in the range of from about 0.5 to about 100 mg/kg, e.g., from about 10 to about 75 mg/kg, of body weight per day, such as 3 to about 50 mg per kilogram body weight of the recipient per day, preferably in the range of 6 to 90 mg/kg/day, most preferably in the range of 15 to 60 mg/kg/day. The compound can be conveniently formulated in unit dosage form; for example, containing 5 mg to 1000 mg, conveniently 10 mg to 750 mg, most conveniently, 50 mg to 500 mg of active ingredient per unit dosage form. In some embodiments, a PAC-1 dosage will be about 50-250 mg/kg, about 75-150 mg/kg, or about 100 mg/kg. In various embodiments, the inhibitor of the BRAF gene or enzyme dosage will be about 0.5 mg/kg to about 25 mg/kg, about 5 mg/kg to about 15 mg/kg, or about 10 mg/kg. MEK inhibitor dosages can be of similar amounts to either of these active agents, or in about one-half to about one-tenth the amount of either of these active agents. In one embodiment, the invention provides a composition comprising an active agent or combination of active agents described herein, formulated in one or more of such unit dosage forms.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by oral administration.

The combination of active agents can be conveniently administered in a unit dosage form, for example, containing 100 to 5,000 mg/m$^2$, 300 to 4,000 mg/m$^2$, 370 to 3,700 mg/m$^2$, 50 to 750 mg/m$^2$, or 750 to 4,000 mg/m$^2$ of active agent per unit dosage form. Each active agent, individually or in combination, can also be administered at about 1 mg/kg to about 250 mg/kg, about 10 mg/kg to about 100 mg/kg, about 10 mg/kg to about 50 mg/kg, about 50 mg/kg to about 100 mg/kg, about 10 mg/kg to about 50 mg/kg, or about 10 mg/kg, about 25 mg/kg, about 50 mg/kg, about 75 mg/kg, about 100 mg/kg, or about 150 mg/kg, or a range from any one of the aforementioned values to any other of the aforementioned values. The active agent can also be administered to a subject to provide a steady-state plasma concentration of the drugs, alone or in combination, of about 1 μmol/L to about 25 μmol/L, or about 10 μmol/L, or about 15 μmol/L.

In some embodiments, the invention provides the active agent in effective concentrations at about 10 nM to about 100 μM. In another embodiment, the effective concentrations are from about 200 nM to about 50 μM, about 500 nM to about 40 μM, about 750 nM to about 25 μM, about 1 μM to about 20 μM, or about 1 μM to about 10 μM. In another embodiment, the effective concentration is considered to be a value such as a 50% activity concentration in a direct procaspase activation assay, in a cell apoptosis induction assay, or in an animal clinical therapeutic assessment. In one embodiment, such value is less than about 200 μM. In another embodiment, the value is less than about 10 μM but greater than about 10 nM. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The active agents described herein can be effective antitumor agents and have higher potency and/or reduced toxicity as compared to the administration of any single agent. The invention provides therapeutic methods of treating cancer in a patient or subject, such as a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma, or leukemia, among others described herein, and in general is characterized by an undesirable cellular proliferation, e.g., unregulated growth, lack of differentiation, local tissue invasion, and metastasis.

The ability of a composition to treat cancer may be determined by using assays well known to the art. For example, the design of treatment protocols, toxicity evaluation, data analysis, quantification of tumor cell kill, and the biological significance of the use of transplantable tumor screens are known. In addition, ability of a composition to treat cancer may be determined using the assays in the citations and patent documents cited herein.

The invention also provides prodrug forms of compounds. Any compound that will be converted in vivo to provide PAC-1 or another active agent recited herein is a prodrug. Numerous methods of forming prodrugs are well known in the art. Examples of prodrugs and methods of preparing them are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, (1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

Additionally, in some embodiments, PAC-1 can be exchanged for a PAC-1 derivative or other inhibitor, such as a compound described in U.S. Pat. No. 7,632,972 (Hergenrother et al.), U.S. Pat. No. 8,778,945 (Hergenrother et al.), or U.S. Pat. No. 8,916,705 (Hergenrother et al.), U.S. Patent Publication Nos. 2007/0049602 (Hergenrother et al.), U.S. application Ser. No. 12/597,287 (Hergenrother et al.), or International Publication No. WO 2014/022858 (Hergenrother et al.), which are incorporated herein by reference. Useful compounds, methods, and techniques for cancer therapy that can be used in combination with the disclosure herein are described in the aforementioned documents, as well as in U.S. Pat. No. 6,303,329 (Heinrikson et al.), U.S. Pat. No. 6,403,765 (Alnemri), U.S. Pat. No. 6,878,743 (Choong et al.), and U.S. Pat. No. 7,041,784 (Wang et al.), and U.S. Patent Publication No. 2004/0180828 (Shi).

Methods for performing the tests and evaluating cancer cell lines can be carried out as described by Putt et al., Nature Chemical Biology 2006, 2(10), 543-550; Peterson et al., J. Mol. Biol. 2009, 388, 144-158; and Peterson et al., Cancer Res. 2010, 70(18), 7232-7241.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

The Combination of Vemurafenib and Procaspase-3 Activation is Synergistic in Mutant BRAF Melanomas The development of vemurafenib resistance limits the long-term efficacy of this drug for treatment of metastatic melanomas with the $^{V600E}$BRAF mutation. Inhibition of downstream MAPK signaling with vemurafenib induces apoptotic cell death mediated by caspase-3, suggesting that addition of a procaspase-3 activator could enhance anticancer effects. Here we show that the combination of PAC-1, a procaspase-activating compound, and vemurafenib is highly synergistic in enhancing caspase-3 activity and apoptotic cell death in melanoma cell lines harboring the $^{V600E}$BRAF mutation. In vivo, the combination displays a favorable safety profile in mice, and exerts significant antitumor effects. We further demonstrate that addition of PAC-1 to the clinically useful combination of vemurafenib and an MEK inhibitor, trametinib, starkly enhances the caspase-3 activity and proapoptotic effect of the combination. Moreover, addition of low concentration PAC-1 also delays the regrowth of cells following treatment with vemurafenib. Finally, PAC-1 remains potent against vemurafenib-resistant A375VR cells in cell culture and synergizes with vemurafenib to exert antitumor effects on A375VR cell growth in vivo. Collectively, our data indicate that inhibition of MAPK signaling combined with concurrent procaspase-3 activation is an effective strategy to enhance the antitumor activity of vemurafenib and mitigate the development of resistance.

Here we report the synergistic activity of PAC-1+vemurafenib and PAC-1+vemurafenib+trametinib in enhancement of caspase-3 activity and apoptotic cell death in $^{V600E}$BRAF melanoma. As a result of increased apoptotic cell death, the PAC-1+vemurafenib combination induces significant reduction in tumor volume in a murine xenograft model of $^{V600E}$BRAF melanoma, well beyond the antitumor effects of the individual agents. In addition, this enhancement of apoptotic death in vemurafenib-sensitive melanoma by the addition of PAC-1 significantly delays the regrowth of cells after exposure to vemurafenib. Finally, PAC-1 remains effective in vemurafenib-resistant A375VR cells in culture and synergizes with vemurafenib to retard tumor growth of these cells in vivo, demonstrating utility of this combination in melanomas that have progressed beyond BRAF-inhibitor treatment, for which few options for treatment are currently available.

Figure 1B:
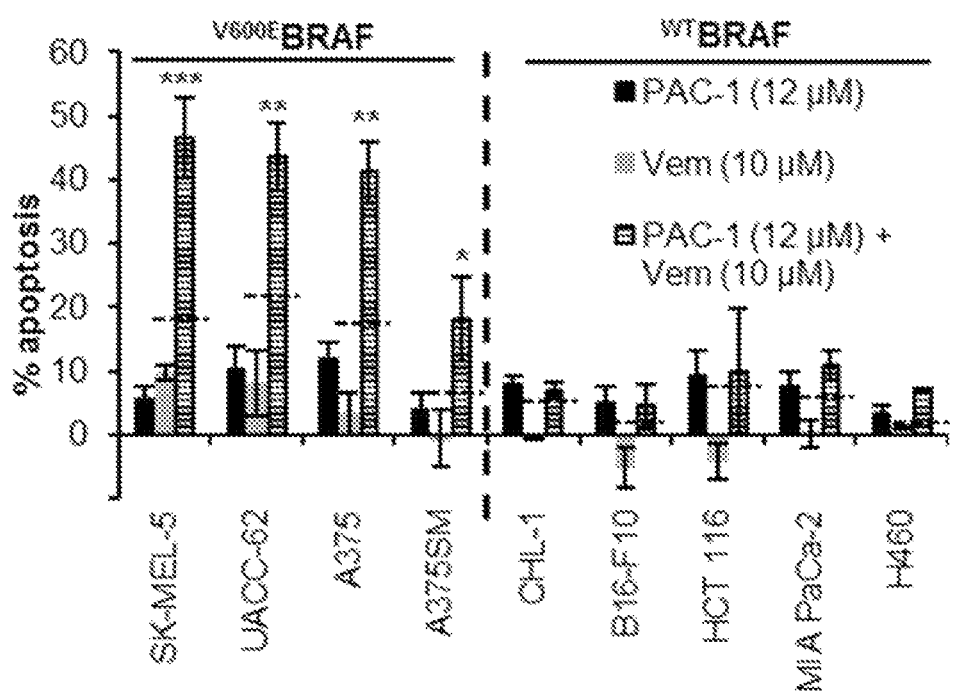
Figure 1C:
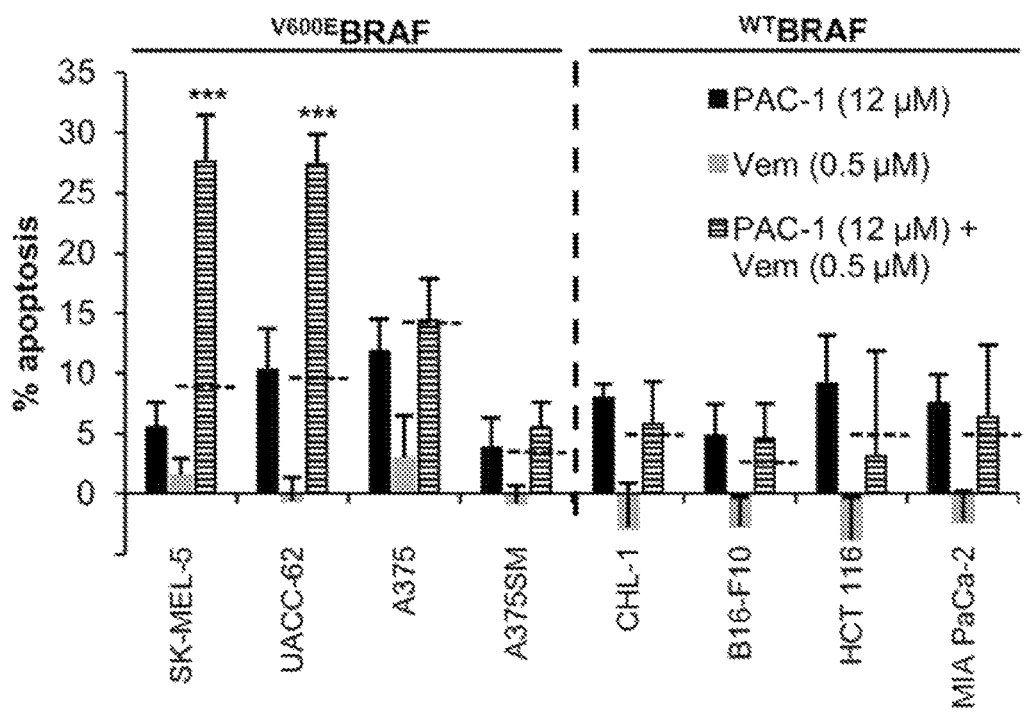

The combination of PAC-1 and vemurafenib enhances apoptosis in cells with the $^{V600E}$BRAF mutation. In a panel of nine cell lines of diverse origins and BRAF mutational status, vemurafenib is potent ($IC_{50}$ values between 200-550 nM) only in cell lines harboring the $^{V600E}$BRAF mutation, consistent with previously reported values (FIG. 1A). Evaluation of PAC-1 in the same panel of cell lines shows that PAC-1 retains similar activity in all cell lines ($IC_{50}$ values between 1-4 µM), regardless of BRAF mutational status (FIG. 1A). The ability of the combination of PAC-1+ vemurafenib to induce apoptotic cell death was then assessed in these cell lines. Under conditions (24 h incubation with compounds) where neither vemurafenib nor PAC-1 induced significant apoptotic death (≤10%) as single agents, the PAC-1+vemurafenib combination induces significant apoptosis (20-45%) in cell lines with the $^{V600E}$BRAF mutation (FIG. 1B). A similar trend was also observed when a lower concentration of vemurafenib (0.5 µM) was evaluated in combination with PAC-1 in $^{V600E}$BRAF cell lines (FIG. 1C). However, the PAC-1+vemurafenib combination does not induce synergistic apoptosis in cell lines with wild-type BRAF (FIG. 1B).

Figure 8A:
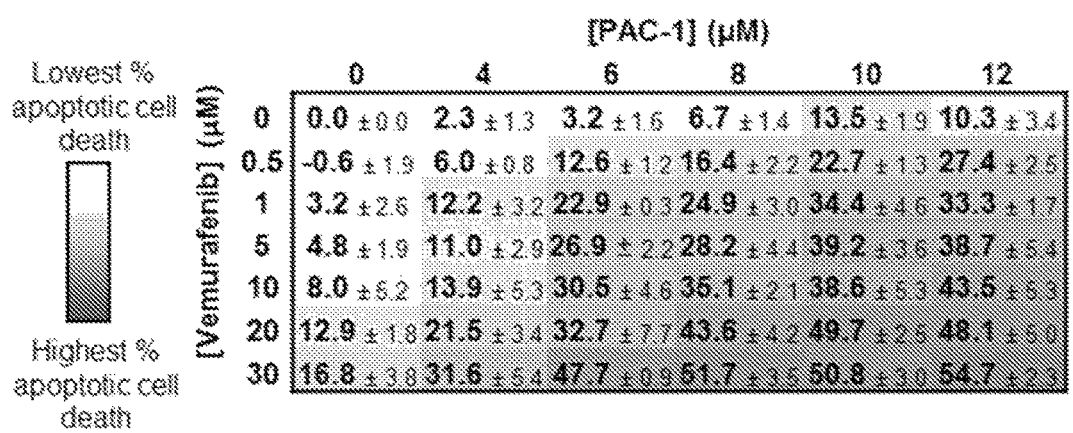

PAC-1 and vemurafenib synergize to enhance caspase-3 activity and apoptosis in A375, SK-MEL-5 and UACC-62 cells. In order to more broadly explore the observed synergy, apoptotic death was assessed in three human $^{V600E}$BRAF melanoma cell lines treated with a matrix of concentrations of PAC-1 and vemurafenib that induce minimal apoptosis as single agents. In these experiments, large increases in the populations of apoptotic cells (beyond the additive effect of single agents alone) were observed in A375 (FIG. 2A), SK-MEL-5 (FIG. 7A) and UACC-62 (FIG. 8A). To quantify the synergy of this drug combination, combination indices (CI) were calculated. A drug combination that is synergistic will have a CI value less than 1, while a value of 1 reflects an additive effect (Chou, *Pharmacol Rev* 2006; 58:621-81). 93% of the calculated CI values are less than 1 (A375 in FIG. 2B, SK-MEL-5 in FIG. 7B and UACC-62 in FIG. 8B), indicating synergism for the combination across all three cell lines tested.

Figure 2A:
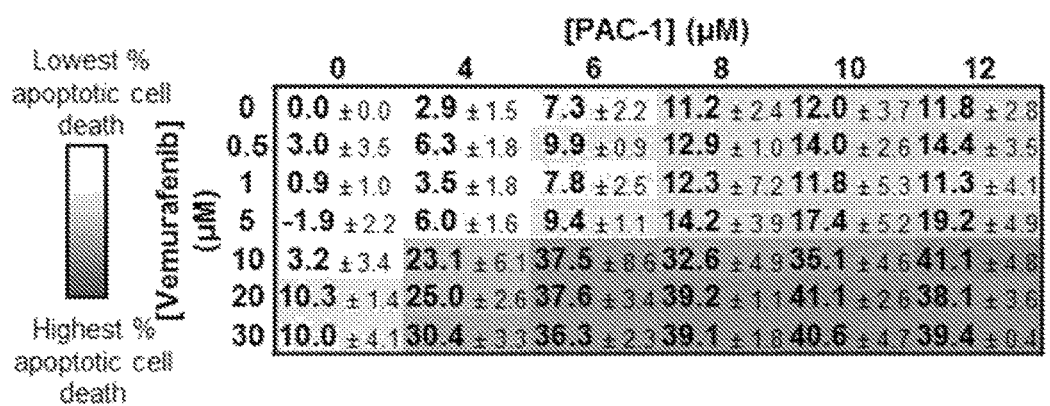
FIGS. 2A-E. PAC-1+vemurafenib powerfully synergize to induce apoptotic death and caspase activity in A375 cells. (A) Shown is percent apoptotic cell death (assessed by Annexin V/PI staining and flow cytometry) induced after 24 h of treatment. Values shown are heat mapped with white representing low % apoptotic cell death and dark gray representing high % apoptotic cell death. (B) Combination indices (CI) calculated for each combination with Combosyn software. CI values are heat mapped with lowest values in light gray and the highest values in black. (C) Significant caspase-3/-7 enzymatic activity is observed in cells treated with the combination of PAC-1 and vemurafenib. PAC-1 (12 µM) and vemurafenib (10 µM) alone have little effect (p-values vs. DMSO control >0.1 at all timepoints). Caspase-3/-7 activity in cell lysates was assessed with the fluorogenic Ac-DEVD-AFC substrate. Activity is expressed as normalized to minimal and maximal activity observed within the assay, with 1 µM staurosporine (STS) as the positive control. P-values shown for 2-way interaction to determine if the combination is different from additive are statistically significant at indicated timepoints. (* $p<0.05$,  $p<0.01$, * $p<0.001$). (D) PAC-1 (12 µM) and vemurafenib (10 µM) alone have little effect on PARP-1 cleavage in A375 cells, but significant PARP-1 cleavage is observed via Western blot with the combination. (E) After 24 h, no/low inhibition of ERK1/2 phosphorylation was observed at low concentrations of vemurafenib (0.1 µM and 0.25 µM). At higher concentrations of vemurafenib (0.5 µM and 1 µM), phosphorylation of ERK1/2 was effectively inhibited with or without addition of PAC-1, indicating that effect of PAC-1 is downstream of the MAPK pathway. However, cleaved PARP-1 was only observed in cells treated with the vemurafenib/PAC-1 combination, even at concentrations of vemurafenib (0.1 and 0.25 µM) where incomplete inhibition of ERK1/2 phosphorylation was observed. Values are reported as mean±SEM of at least three experiments.
Figure 2B:
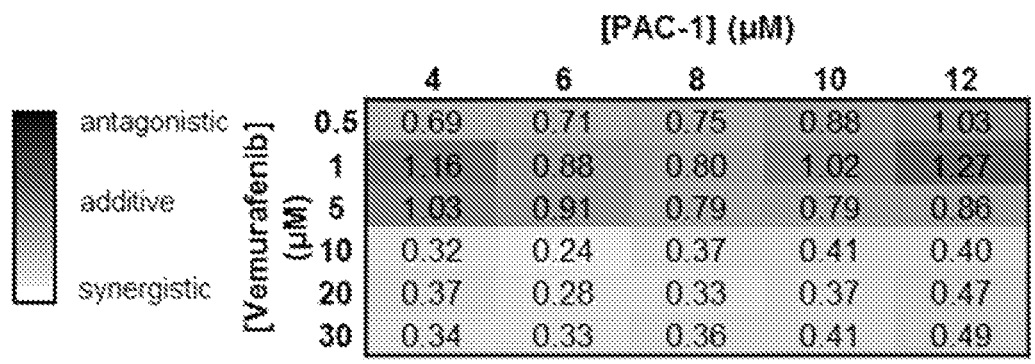
Figure 2C:
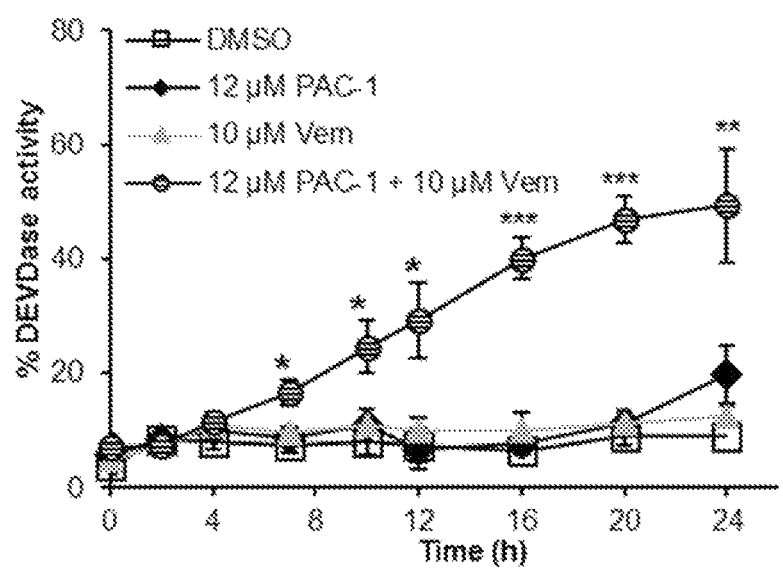
Figure 2D:
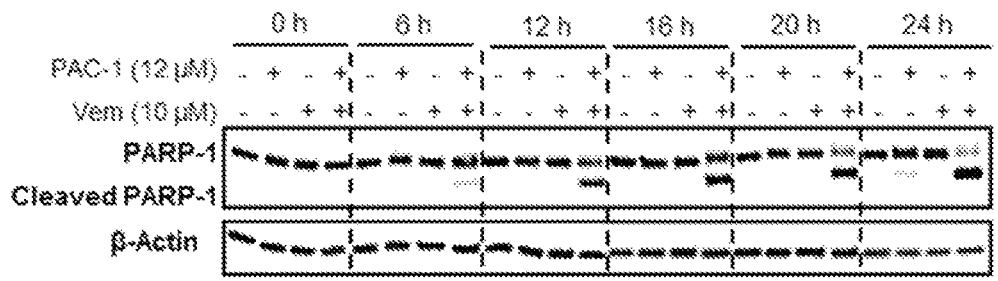
Figures 8B, 8C:
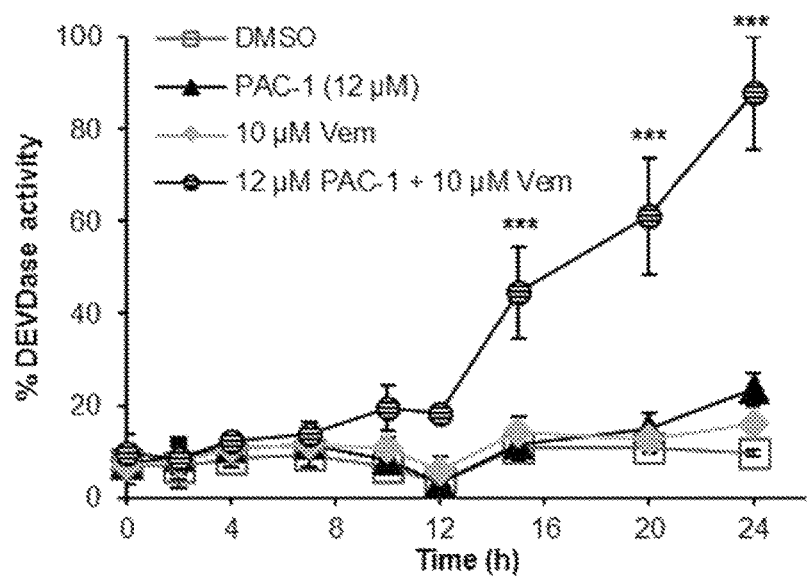
Figure 8D:
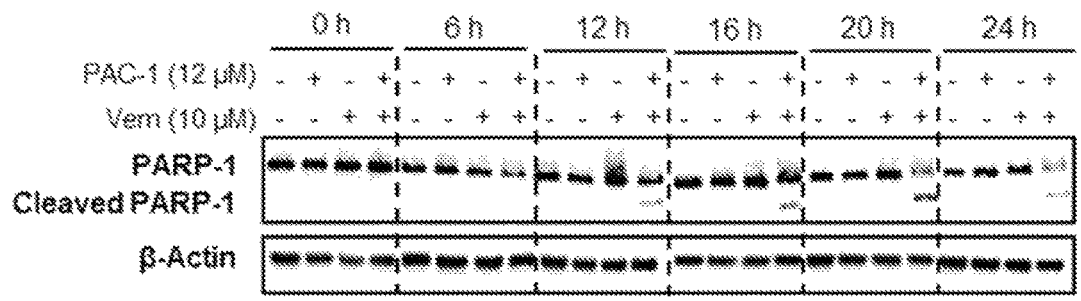

To assess if the increase in apoptosis was a result of increased activation of executioner procaspases, caspase-3/-7 enzymatic activity was evaluated in A375 cells (after lysis) using a fluorogenic substrate. In A375 cells treated with vemurafenib or PAC-1 alone (at the same concentrations used in FIG. 1B), negligible increases in caspase-3 activity were observed at these time points and concentrations (FIG. 2C). However, when A375 cells were treated with PAC-1 and vemurafenib, a significant increase in caspase-3 activity was observed as early as 7 h posttreatment (FIG. 2C). In Western blot analyses, neither of the single agents had an effect on PARP-1 cleavage at these time points and concentrations; however, the combination resulted in significant cleaved PARP-1 (FIG. 2D), a result of the increased caspase-3/-7 activity in cells treated with the PAC-1+vemurafenib combination. After treatment with the combination for 24 h, near-complete cleavage of PARP-1 was observed in A375 cells (FIG. 2D). Similar results for the caspase-3/-7 activity assay and cleavage of PARP-1 were also observed in SK-MEL-5 (FIGS. 7C and 7D) and UACC-62 cells (FIGS. 8C and 8D).

The PAC-1 derivative PAC-1a lacks the zinc chelating motif and thus does not activate procaspase-3 or induce apoptosis.

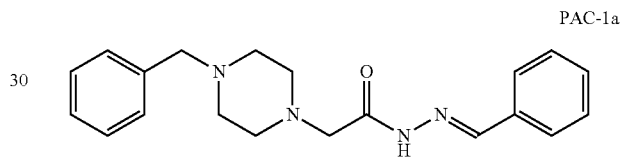

PAC-1a

Figure 9A:
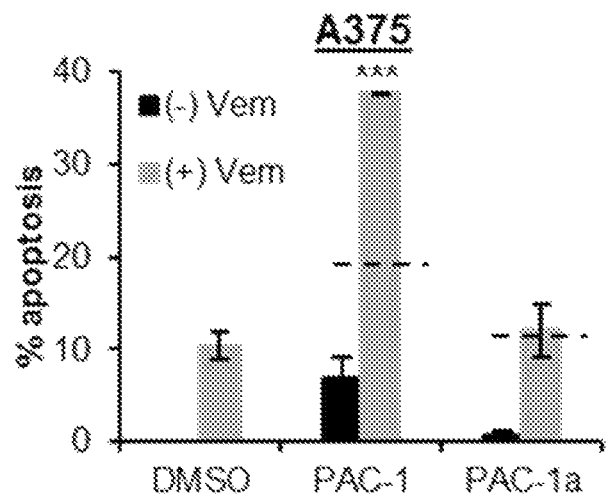
Figure 9B:
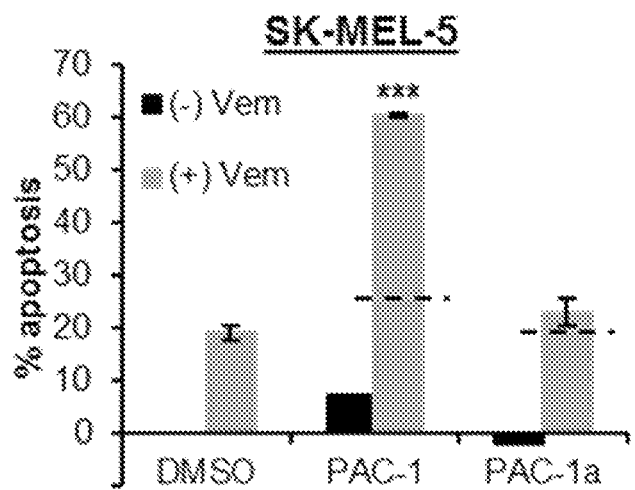
Figure 9C:
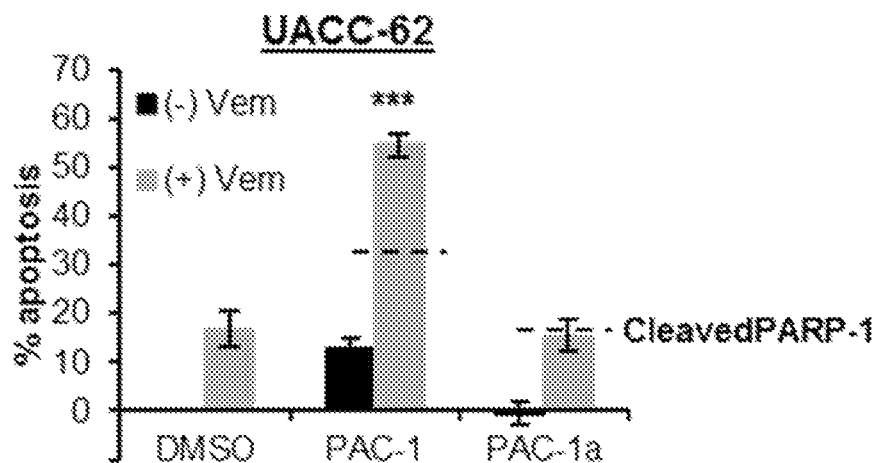
Figure 9D:
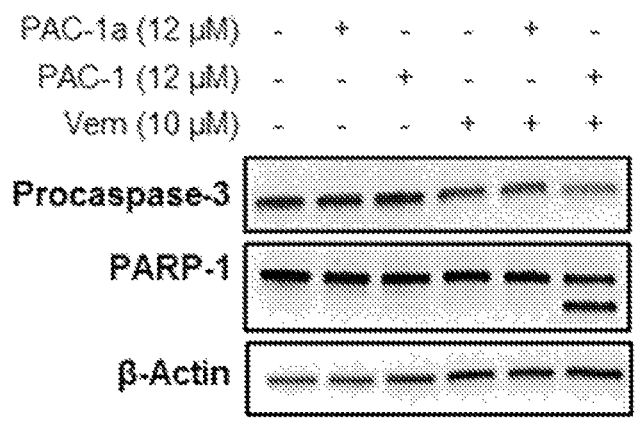

Use of PAC-1a in combination with vemurafenib did not result in a significant increase in the proportion of cells undergoing apoptosis in A375, SK-MEL-5 or UACC-62 cells (FIG. 9A-C). This result is also consistent with the absence of increased PARP-1 cleavage in cells treated with the PAC-1a and vemurafenib combination (FIG. 9D), indicating that the cells did not undergo apoptotic death.

Inhibition of ERK1/2 phosphorylation and activation of procaspase-3 are required to enhance apoptotic cell death. Consistent with the data in FIG. 1B, no enhancement in caspase-3 activity or PARP-1 cleavage were observed in two $^{WT}$BRAF cell lines when treated with the combination of PAC-1+vemurafenib (FIG. 1A-C). The lack of PAC-1+ vemurafenib synergy in cell lines harboring $^{WT}$BRAF suggests that inhibition of ERK1/2 and activation of procaspase-3 are both required to induce the dramatic enhancement of apoptotic cell death. Indeed, after 24 h of treatment with vemurafenib, inhibition of ERK1/2 phosphorylation was not observed in $^{WT}$BRAF cell lines even at high concentrations (30 µM) of vemurafenib (FIGS. 1B and 1C). This observation is consistent with previous reports where vemurafenib does not inhibit ERK1/2 phosphorylation in $^{WT}$BRAF cells, but paradoxically activates it.

Figure 2E:
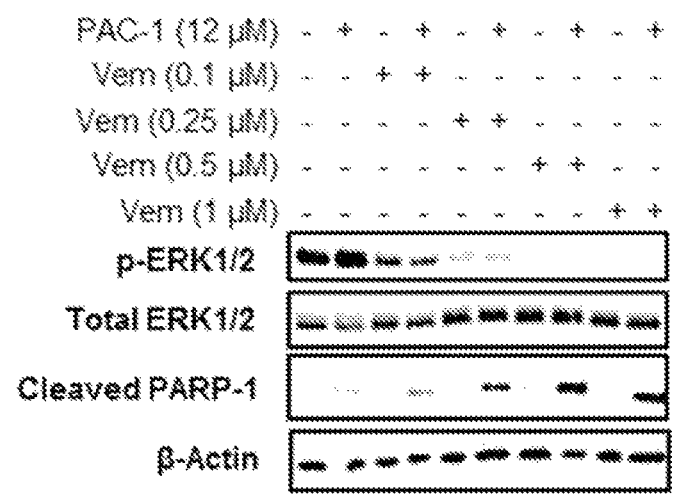
Figure 8E:
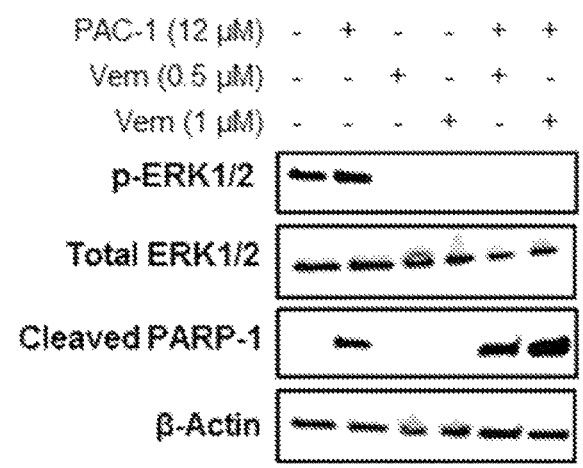

To further investigate this, A375 (harboring $^{V600E}$BRAF) cells were treated with PAC-1, vemurafenib, or the combination and probed for the presence of cleaved PARP-1 and ERK1/2 phosphorylation. After 24 h, phospho-ERK1/2 bands were not observed in cells treated with vemurafenib (at 0.5 and 1.0 µM) and the combination (FIG. 2E). However, significant increases in the amount of cleaved PARP-1 were only observed in cells treated with both PAC-1 and vemurafenib (FIG. 2E). Similar results were also observed in SK-MEL-5 (FIG. 7E) and UACC-62 cells (FIG. 8E). At low concentrations of vemurafenib (0.1 and 0.25 µM), where incomplete inhibition of ERK1/2 phosphorylation was observed, slight increase in PARP-1 cleavage over that single agent effects was also observed (FIG. 2E). This result suggests that even with incomplete inhibition of ERK1/2 phosphorylation, procaspase-3 activation, which is downstream of ERK1/2 signaling, can be enhanced with the addition of PAC-1 to vemurafenib treatments. Taken together, the data show that procaspase-3 activation via PAC-1 dramatically enhances the proapoptotic effect of vemurafenib in cell lines with $^{V600E}$BRAF mutation.

Figure 3A:
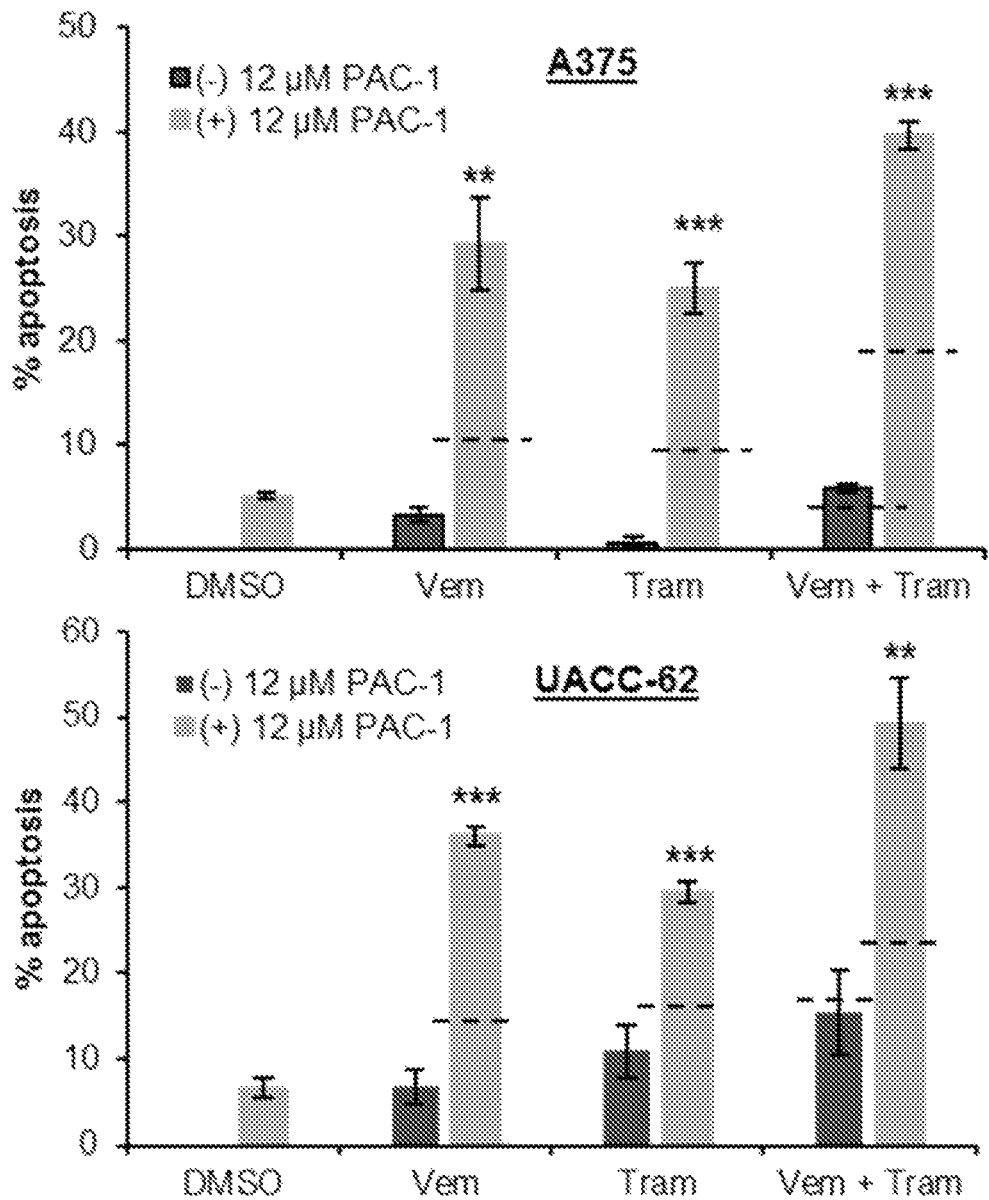
FIGS. 3A-C. Addition of PAC-1 to the combination of vemurafenib+trametinib powerfully synergizes to induce apoptotic death and caspase activity in A375 and UACC-62 cells. (A) Shown is percent apoptotic cell death after 24 h of treatment. Combination of trametinib (100 nM) and vemurafenib (10 µM) leads to a minimal increase in the population of apoptotic cells. Addition of PAC-1 (12 µM) leads to a dramatic increase in the population of apoptotic cells that is beyond the additive effect of the three agents. (B) Trametinib (100 nM) and vemurafenib (10 µM) in combination have little effect on PARP-1 cleavage in A375 and UACC-62 cells, but significant PARP-1 cleavage and reduction in procaspase-3 level are observed via Western blot with the addition of PAC-1 (12 µM). (C) Combination of vemurafenib and trametinib lead to additive increase in caspase-3/-7 activity but addition of PAC-1 leads to significant increases in caspase-3/-7 enzymatic activity in A375 and UACC-62 after 24 h. PAC-1 (12 µM), vemurafenib (10 µM) and trametinib (100 nM) alone have little effect (p-values vs. DMSO control >0.1). Activity is expressed as normalized to the positive control. Dashed horizontal lines represent the level of cell death expected from a mere additive effect of the two agents. Values are reported as mean±SEM of at least three experiments. P-values shown for 2-way interaction to determine if the combination for induction of apoptosis is different from an additive effect of individual agents are statistically significant (* $p<0.05$,  $p<0.01$, * $p<0.001$).
Figure 3B:
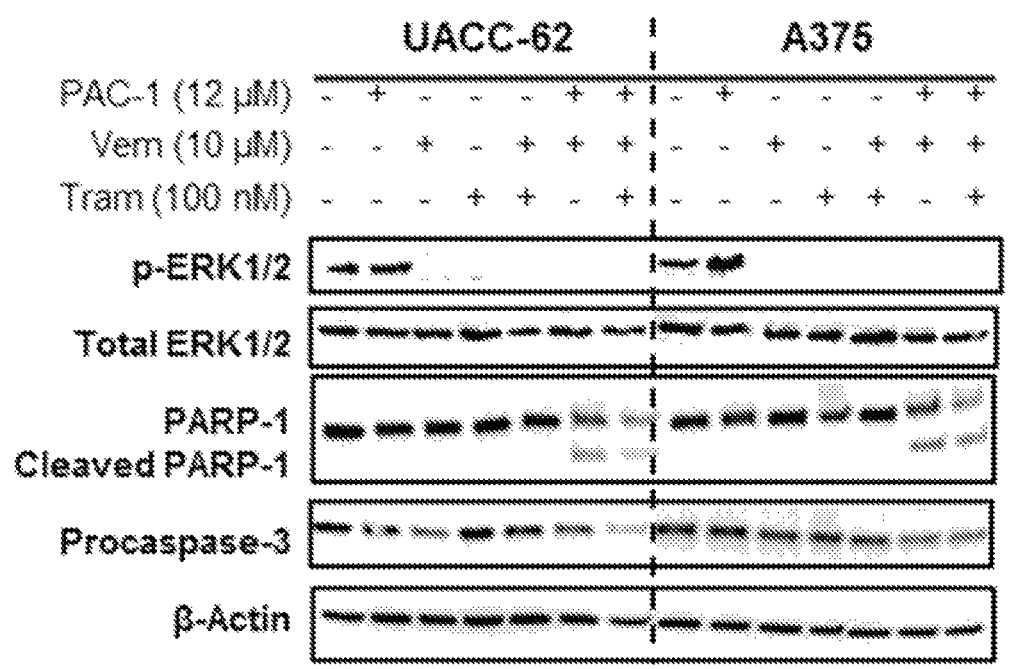
Figure 3C:
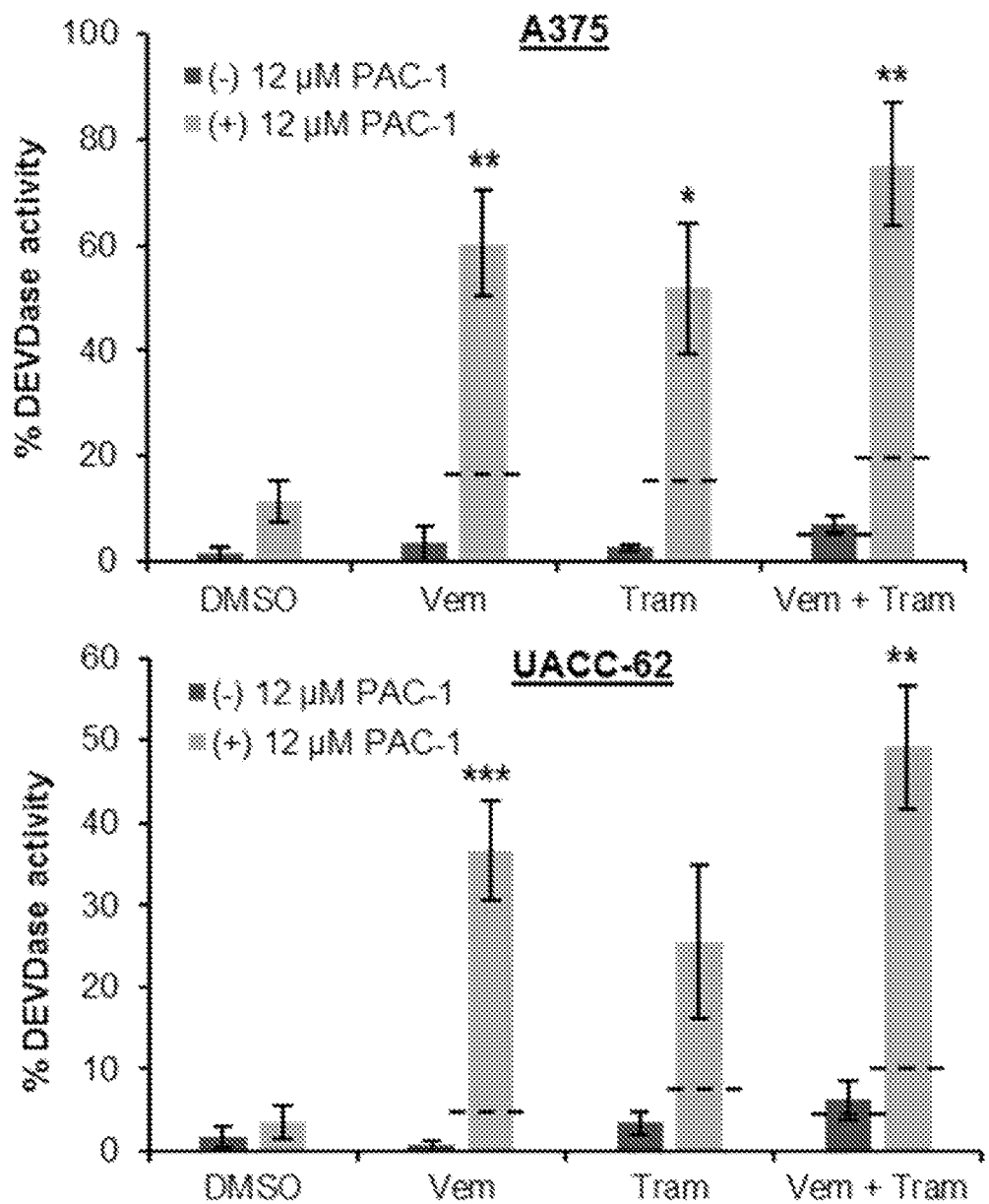

Addition of PAC-1 to vemurafenib and trametinib enhances caspase-3 activity and apoptosis. Addition of a MEK1/2 inhibitor, such as trametinib, is widely used in the clinic to enhance the efficacy of vemurafenib in $^{V600E}$BRAF melanomas. To explore the effect of PAC-1 with this combination, cells were treated with vemurafenib+trametinib, in the presence or absence of PAC-1, and apoptosis was assessed. In both A375 and UACC-62 cell lines, vemurafenib+trametinib co-treatment led to mere additive increases in the population of apoptotic cells (FIG. 3A). In contrast, the addition of PAC-1 led to a large increase in the population of apoptotic cells, beyond the additive effect of single agents alone (FIG. 3A). Vemurafenib+trametinib co-treatment did not lead to PARP-1 cleavage, while addition of PAC-1 led to near quantitative cleavage of PARP-1 (FIG. 3B). To explore if the increased apoptotic cell death in the presence of PAC-1 is a result of enhanced enzymatic activity of executioner caspases, the caspase-3/-7 activity of A375 and UACC-62 cells treated with vemurafenib+trametinib, plus or minus PAC-1, was assessed. Again, a dramatic increase in caspase-3/-7 activity was observed when PAC-1 was included, an effect that was absent without addition of PAC-1 (FIG. 3C).

Figure 4A:
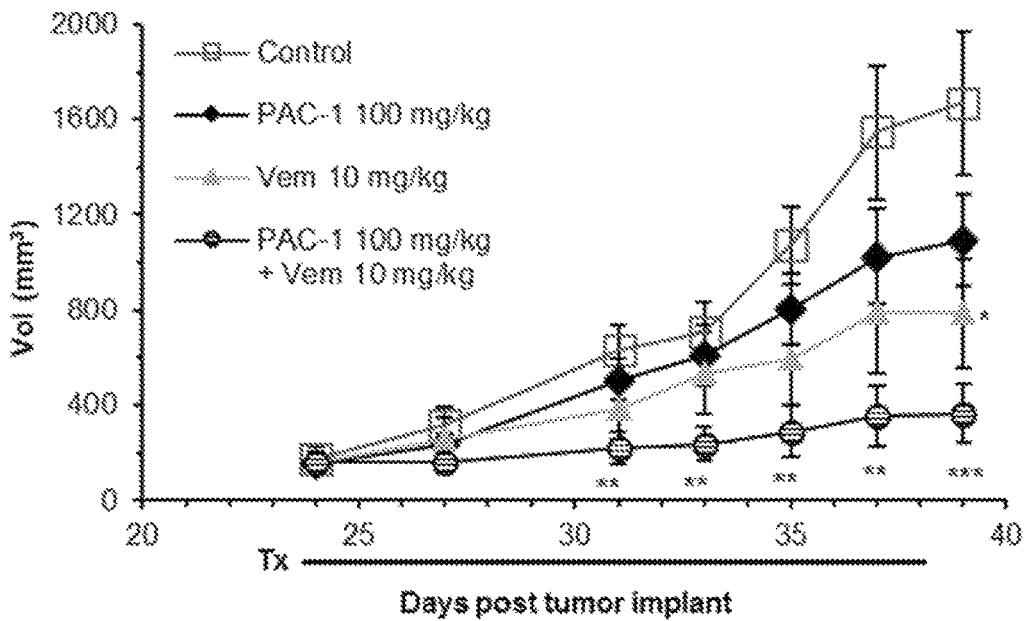
FIGS. 4A-E. The PAC-1+vemurafenib combination retards tumor growth in an A375 subcutaneous mouse xenograft model of melanoma. (A) The effect of PAC-1, vemurafenib, and their combination in the A375 model. Mice bearing subcutaneous tumors were dosed for 15 days. Mice were dosed with PAC-1 once daily at 100 mg/kg (n=6) via i.p. injection, vemurafenib twice daily at 10 mg/kg (n=8) by (p.o.), or the PAC-1+vemurafenib combination (n=8). The black line below the x-axis indicates the dosing period for the mice during the study. Tumor volumes are plotted as mean±SEM. (B) Masses of the excised tumors. (C) Tumor lysates were analyzed by Western blot for changes in procaspase-3 levels. Actin was used as loading control. Band intensity was quantified using ImageJ. (D) Plot of procaspase-3 levels normalized to the actin loading controls. (E) Percentage of cells that are positive for Ki-67 following immunohistochemical staining of formalin fixed tumor samples. 2000 cells were counted in each sample for each of the four treatment groups. P-values shown are with respect to control mice. (* $p<0.05$,  $p<0.01$, * $p<0.001$).
Figure 4B:
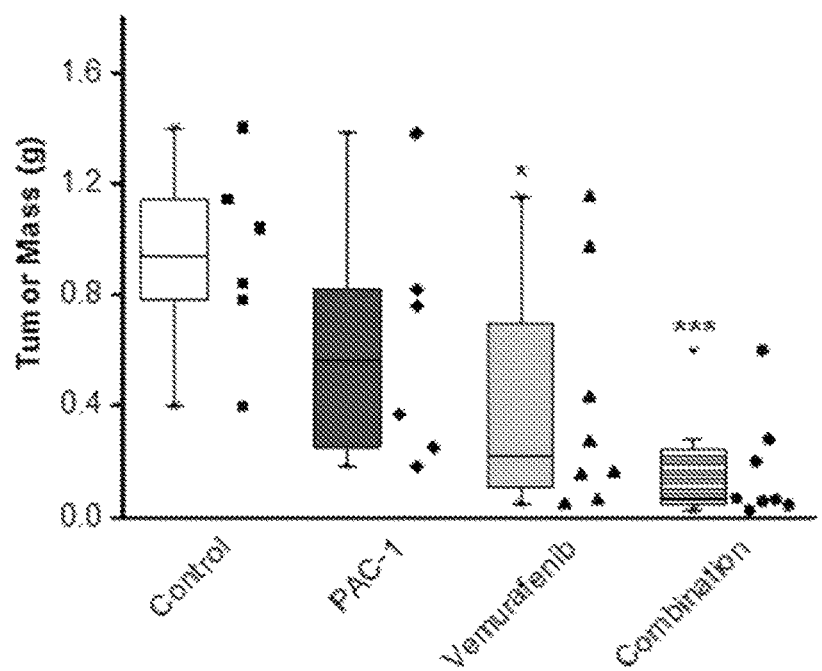

The combination of vemurafenib and PAC-1 significantly reduces tumor burden in an A375 xenograft model. To determine the antitumor effect of the PAC-1+vemurafenib combination in vivo, an A375 xenograft model (Yadav et al., Mol Cancer Ther 2014; 13:2253-63) was used. In this model, nude mice were inoculated subcutaneously with A375 cells, and after allowing the tumors to grow, mice were randomized based upon tumor volume into four groups [F=0.03<$F_{critical}$(3.01)] and dosed with PAC-1, vemurafenib, or the combination for 15 days. Treatment with PAC-1 alone led to minimal reduction in tumor mass and volume compared to untreated control mice (FIGS. 4A and 4B). Mice dosed with vemurafenib alone experienced a moderate reduction (53%; p=0.04) in tumor volume and mass compared to control (FIGS. 4A and 4B), with 3 out of 8 mice having comparable tumor mass as the control mice (FIG. 4B). In contrast, mice treated with the combination of PAC-1 and vemurafenib had significantly smaller tumor burden compared to control mice (FIG. 4A, 4B and FIG. 11). In these mice, a 78% reduction in tumor volume was observed (FIG. 4A, p=0.0008 vs. control), with 6 out of 8 mice having tumors less than 0.2 g in mass (FIG. 4B), indicating that addition of PAC-1 enhances the antitumor effects of vemurafenib in vivo and reduces the variability in response to treatment.

Figure 4C:
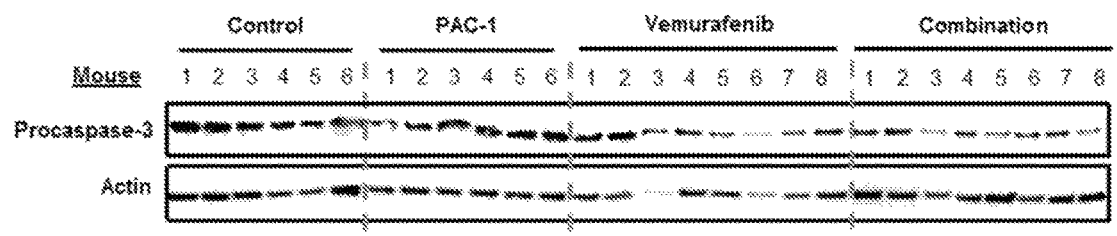
Figure 4D:
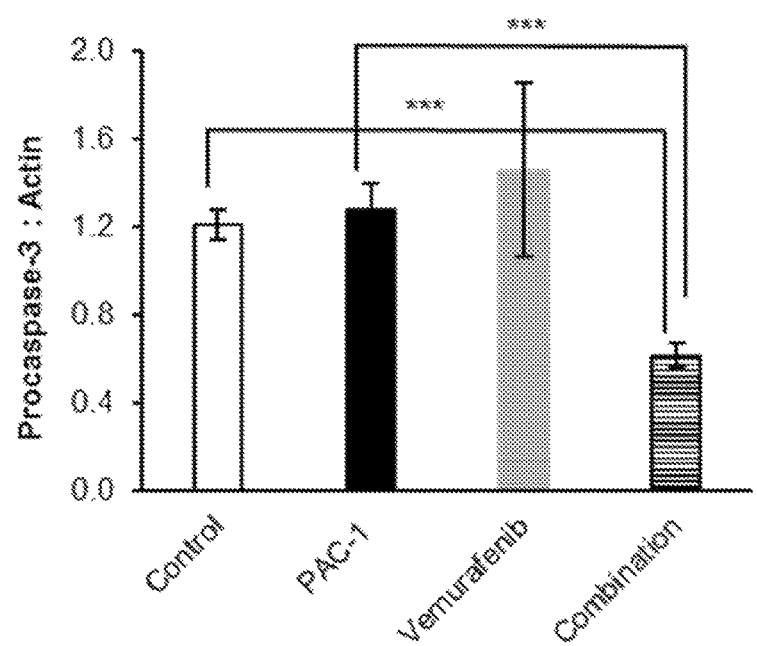
Figure 4E:
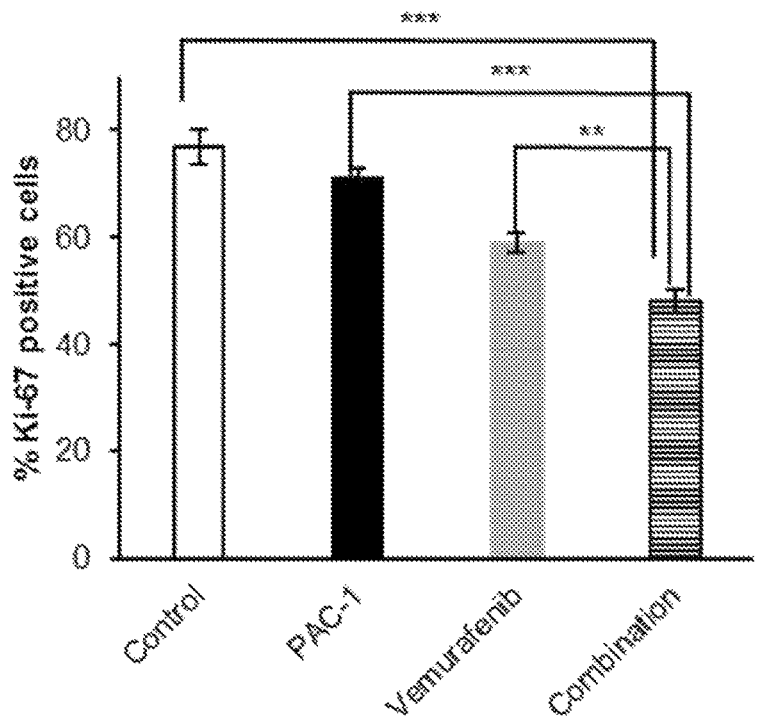

Examination of procaspase-3 levels in the tumor samples by Western blot showed an appreciable and consistent reduction in the amount of procaspase-3 only in tumor samples derived from mice that received the combination treatment, versus variable responses for the other dosing groups (FIGS. 4C and 4D). Using immunohistochemical staining, a significant reduction in the percentage of Ki-67 expressing cells in tumors treated with PAC-1+vemurafenib was observed (FIG. 4E), indicating that the PAC-1+vemurafenib combination was capable of not only amplifying procaspase-3 activation, but also attenuating cell proliferation. Finally, in mice treated with PAC-1+vemurafenib, no hematological toxicities were observed (Table 1), indicating a favorable safety profile for the combination. Taken together, the in vivo data are consistent with the cell culture results showing that the synergy of PAC-1+vemurafenib leads to increase in caspase-3 activity and induction of apoptotic cell death, as well as reduction in cell proliferation.

TABLE 1

Hematologic and biochemical toxicity of PAC-1 and vemurafenib. Average data from 4 mice treated with 100 mg/kg PAC-1 once-a-day and 10 mg/kg vemurafenib twice-a-day for 15 days. No clinically significant evidence for myelosuppression, renal injury, or hepatic toxicity was identified.

| Blood chemistry | Ave ± SEM | Normal Range[1] |
|---|---|---|
| Creatinine (mg/dL) | 0.20 ± 0.04 | 0.2-0.4 |
| BUN (Urea) (mg/dL) | 32.3 ± 1.0 | 11-39 |
| Total Protein (g/dL) | 4.7 ± 0.1 | 4.8-6.6 |
| Albumin (g/dL) | 2.2 ± 0.1 | 2.8-4.0 |
| Globulin (g/dL) | 2.5 ± 0.1 | |
| Calcium (mg/dL) | 9.2 ± 0.2 | 9.5-12.1 |
| Phosphorous (mg/dL) | 10.8 ± 0.5 | 8.0-15.5 |
| Sodium (mmol/L) | 161.0 ± 0.8 | 140.7-165.1 |
| Potassium (mmol/L) | 7.9 ± 0.2 | 7.0-10.8 |
| Chloride (mmol/L) | 119.0 ± 0.9 | 108.8-133.2 |
| Glucose (mg/dL) | 182.3 ± 12.5 | 149-271 |
| Alkaline Phos Total (U/L) | 70.8 ± 9.0 | 76-301 |
| ALT (SGPT) (U/L) | 50.5 ± 4.6 | 31-115 |
| Total Bilirubin (mg/dL) | 0.3 ± 0.1 | 0.2-0.5 |
| Cholesterol total (mg/dL) | 111.5 ± 4.4 | 98-202 |
| Platelet Estimate* ($10^3$/µL) | 229.3 ± 7.5 | 376-1796 |
| WBC Estimate ($10^3$/µL) | 3.2 ± 0.4 | 1.4-10.3 |
| Seg % | 31.5 ± 8.7 | 14.0-54.7 |
| Lymph % | 61.5 ± 9.6 | 23.6-79.3 |

*Platelet cell counts were low because platelet clumps were observed.
[1]Normal range values were obtained from Charles River for female NU/NU mice between 8 to 10 weeks of age.

Figure 5A:
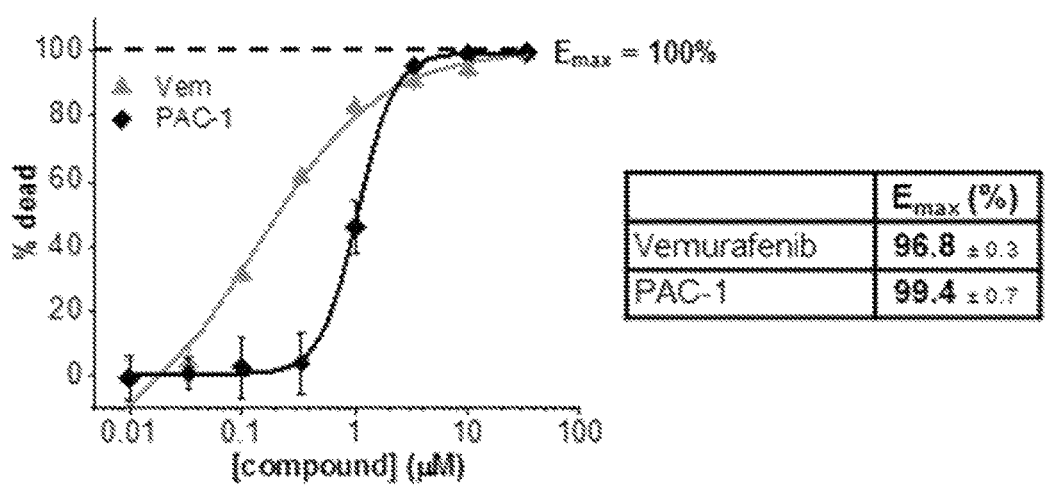
FIGS. 5A-D. Low concentrations of PAC-1 (1 µM) significantly delay cell regrowth in combination with vemurafenib in long-term cell culture experiments. (A) Comparison of $E_{max}$ values in A375 cells treated with vemurafenib and PAC-1. (B) A375 and SK-MEL-5 cells treated with PAC-1 (4 µM) or vemurafenib (10 µM) for a duration of 30 days. (C) A375 cells were treated with PAC-1 (1 µM), vemurafenib (5 µM or 10 µM), or the combination. After 5, 10 or 20 days, the wells were fixed with 10% trichloroacetic acid, stained with 0.5% sulforhodamine B (SRB) dye, and imaged with BioRad GelDoc RX. Day 20 images of control and PAC-1 samples are not shown because the cells were unviable due to overcrowding. (D) Quantification of (C) where the SRB dye is dissolved in 10 mM Tris base at pH 10.4, and the absorbance read at 510 nm. Corrected absorbance at 510 nm was plotted against the days of continuous treatment by normalizing against absorbance on Day 0 before the start of treatment. Values are reported as mean±SEM of at least three experiments. T-test performed between wells treated with vemurafenib only versus vemurafenib and PAC-1 (1 µM). On day 10, only the wells treated with vemurafenib (10 µM) and PAC-1 (1 µM) are significantly different from vemurafenib (10 µM) only (p=0.049) treatment. On day 20, wells treated with vemurafenib (5 or 10 µM) and PAC-1 (1 µM) are significantly different from vemurafenib (5 or 10 µM), as indicated. (* $p<0.05$,  $p<0.01$, * $p<0.001$).
Figure 5B:
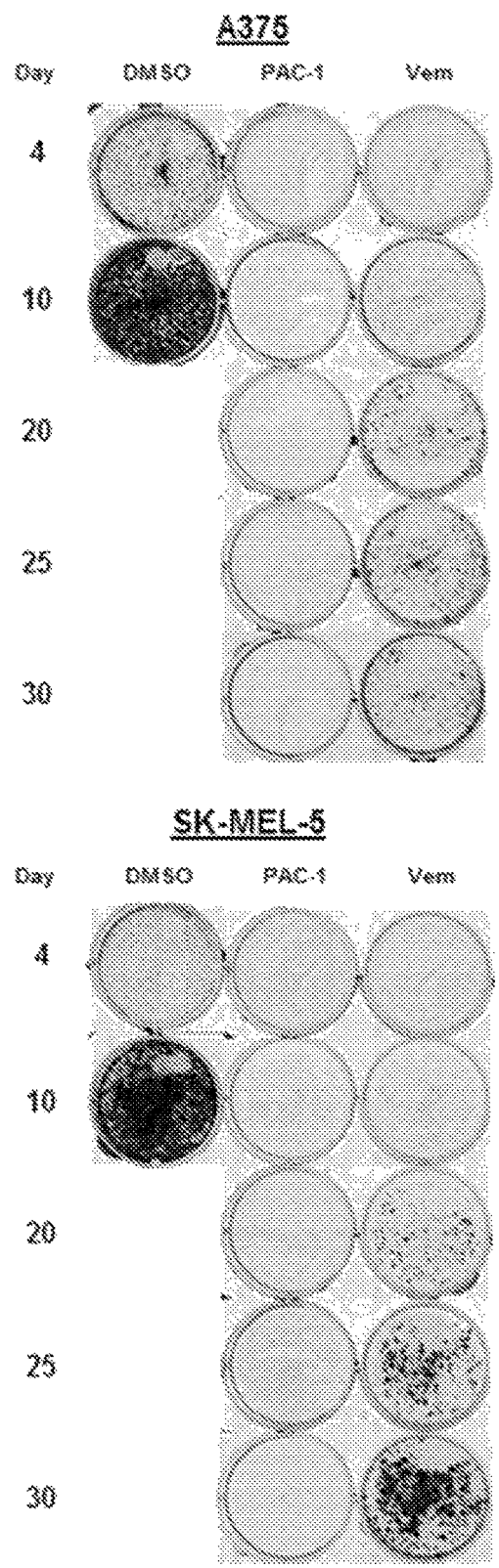

Long term treatment with PAC-1 prevents cell regrowth, and addition of PAC-1 to vemurafenib delays the onset of cell regrowth. The $E_{max}$ of vemurafenib (the percent cell death induced by high concentrations of compound) in A375 cells is 96.8±0.3% after 5 days (FIG. 5A), indicating that ~3% of A375 cells are insensitive to vemurafenib. Under the same conditions, PAC-1 has an $E_{max}$ of 99.4±0.7% (FIG. 5A), indicating that PAC-1 kills A375 cells quantitatively, with very few insensitive cells. We therefore hypothesized that long term treatment with vemurafenib would lead to re-growth of cancer cells, while treatment with PAC-1 should prevent re-growth. To investigate this hypothesis, A375 and SK-MEL-5 cells were plated at low densities and treated continuously with PAC-1 (4 µM) or vemurafenib (10 µM) for up to 30 days. In A375 and SK-MEL-5 cells treated with vemurafenib, regrowth of cells was observed in as early as 20 days (FIG. 5B). However, in wells treated with PAC-1, no regrowth was observed even after 30 days (FIG. 5B). Thus, consistent with the higher $E_{max}$ value, PAC-1 is able to quantitatively kill cells thereby preventing regrowth.

Figure 5C:
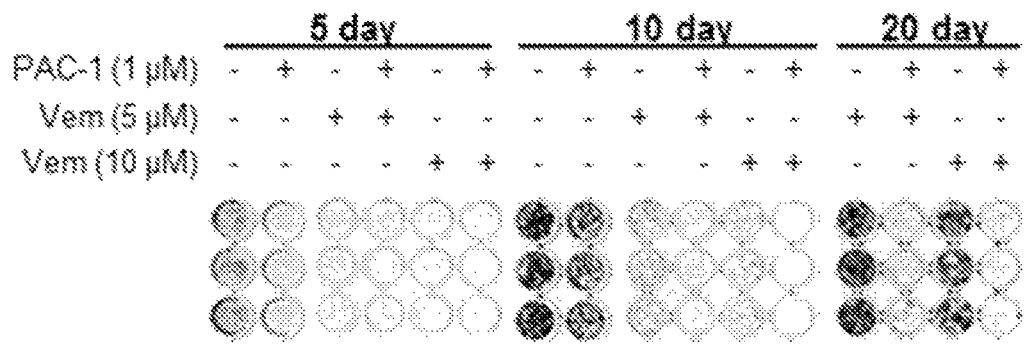
Figure 5D:
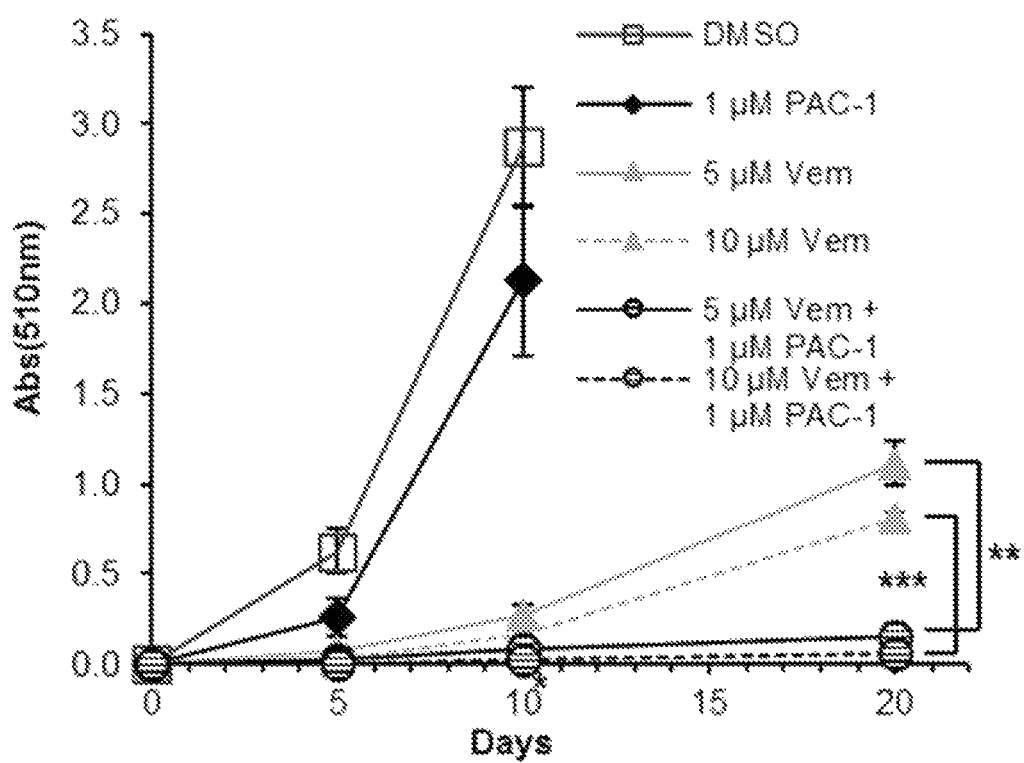

To investigate if addition of low concentrations of PAC-1 could combine with vemurafenib to prevent cancer cell re-growth, A375 and UACC-62 cells were plated at low densities in 96-well plates and treated continuously with PAC-1 (1 µM), vemurafenib (5 µM or 10 µM), or the combination for up to 20 days. After 5 days, treatment with PAC-1, vemurafenib, or the combination each resulted in significant reduction in cell number compared to the control (A375: FIGS. 5C and 5D; UACC-62: FIGS. 12A and 12B). On day 10, there is no observable difference between the PAC-1 treated wells and the control. In wells treated with 5 µM or 10 µM vemurafenib, cell death was 89.4±1.4% and 93.2±1.1%, respectively. However, in wells where A375 cells were treated with 1 µM PAC-1 and 5 µM or 10 µM vemurafenib, increased cell death was observed, 96.1±1.0% and 97.9±0.7% respectively. Consequent to achieving more complete cell death, a smaller proportion of cells remain in wells treated with both PAC-1 and vemurafenib. After 20 days of treatment, significant regrowth of colonies was observed in vemurafenib-only treated wells but not in wells receiving the co-treatment (A375: FIGS. 5C and 5D; UACC-62: FIGS. 12A and 12B). This result indicates that the more complete cell death induced by co-treating cells with PAC-1 and vemurafenib is effective in delaying the regrowth of A375 and UACC-62.

PAC-1 synergizes with vemurafenib in vemurafenib-resistant melanoma in vivo. To assess if PAC-1 remains active in a cell line that has acquired resistance to vemurafenib, a vemurafenib-resistant A375VR cell line was generated by growing A375 parental cell line in sequentially higher concentrations of vemurafenib (0.5 µM to 1.0 µM) for 2 months. To determine the mechanism of resistance of A375VR, genes for MEK1/2, NRAS and AKT were sequenced, but no commonly reported mutations that would confer resistance were found (Rizos et al., *Clinical Cancer Research* 2014; 20:1965-77). Similarly, splice variant of the $^{V600E}$BRAF mRNA was also not observed. Through qPCR, A375VR cells have approximately 3-fold higher levels of MDR1 mRNA compared to A375. However, compared to up to 1000-fold higher levels of MDR1 mRNA in ovarian cells resistant to doxorubicin or cisplatin, the level of MDR1 mRNA overexpression is considered low, indicating that resistance is unlikely due to dramatic upregulation of MDR phenotype.

Figure 6A:
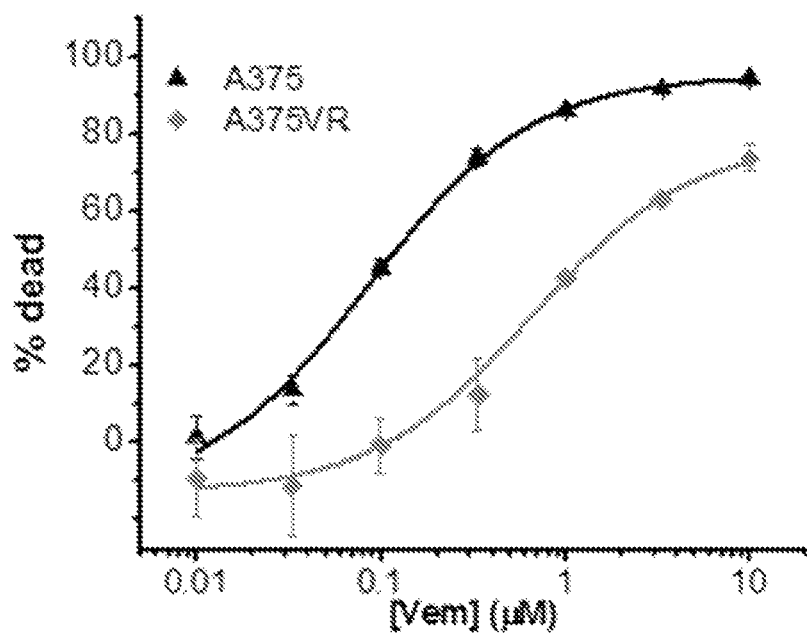
Figure 6B:
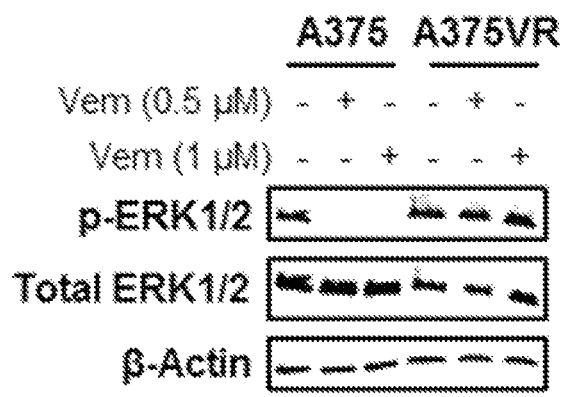
Figure 6C:
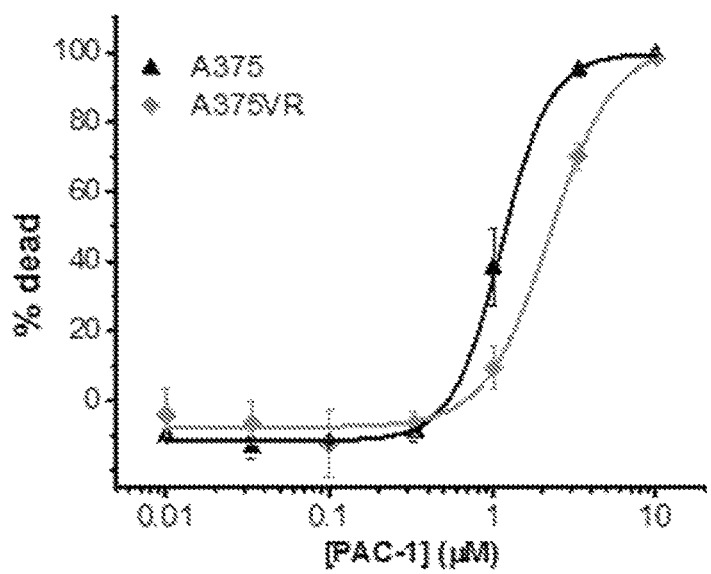
Figure 6D:
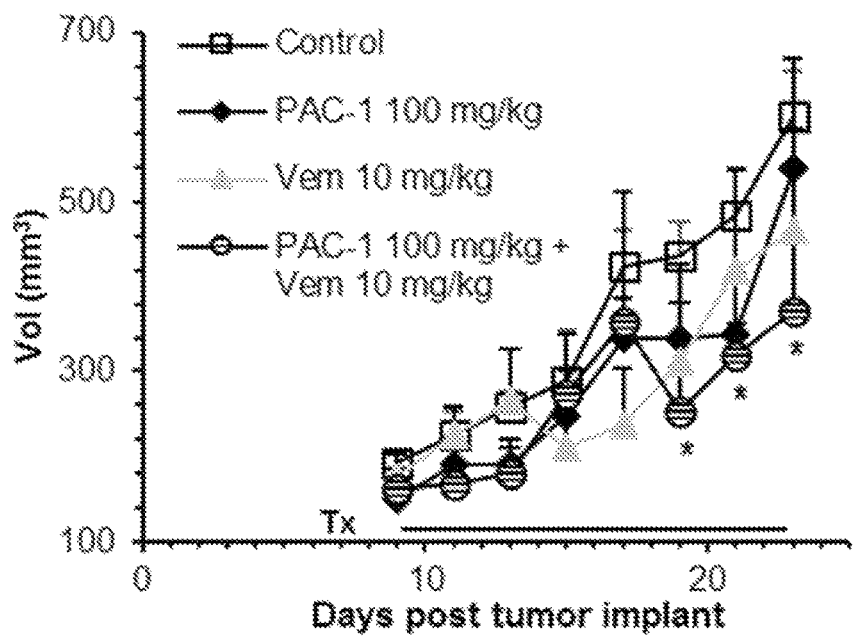
Figure 7A:
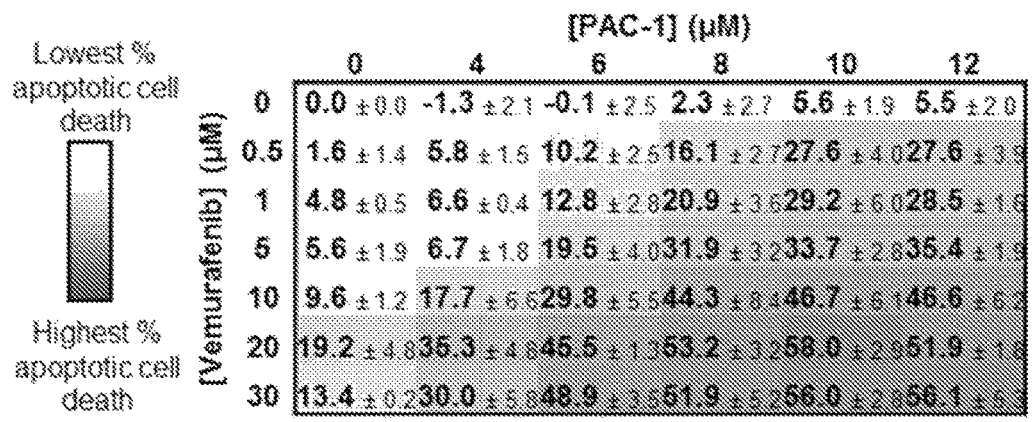
Figure 7B:
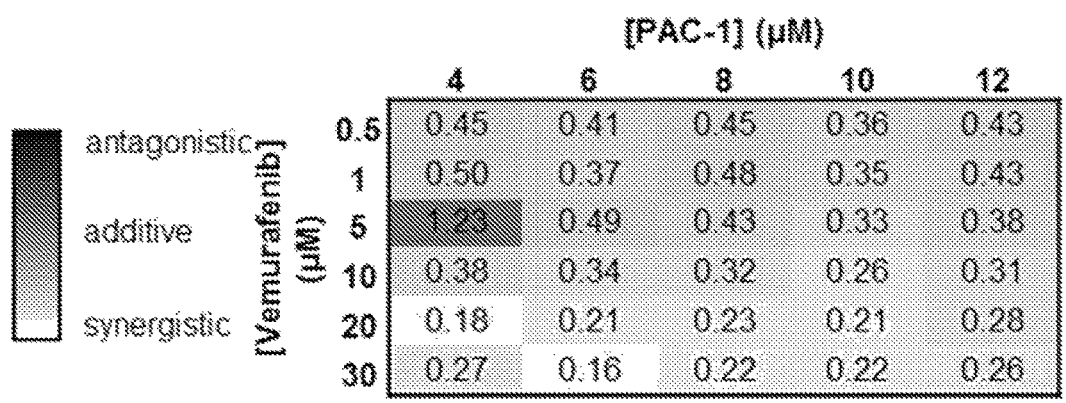
Figure 7C:
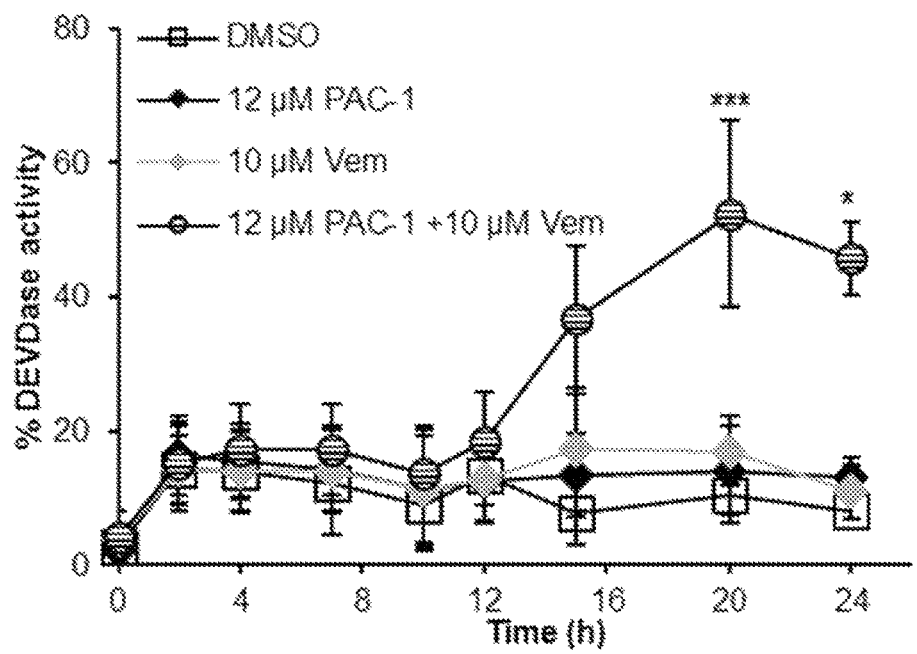
Figure 7D:
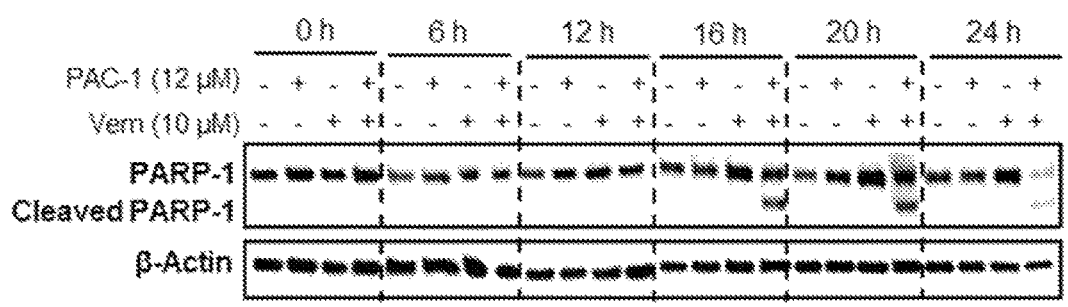
Figure 7E:
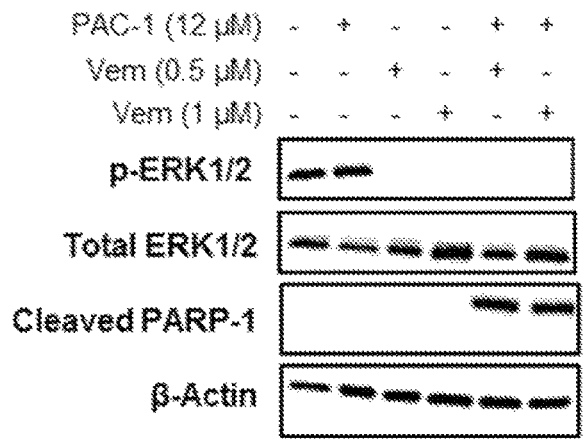

Vemurafenib kills the A375VR cell line with a 5-day $IC_{50}$ value of 1.5 µM, 12-fold less potent compared to the sensitivity of the parental A375 (FIG. 6A). Moreover, the vemurafenib $E_{max}$ for A375VR is 79±6.3%, which is 14% lower than the parental A375 cell line. While treatment of parental A375 cells with vemurafenib (0.5 or 1 µM) for 2 h results in complete inhibition of ERK1/2 phosphorylation, this effect is not observed in A375VR, consistent with resistance of A375VR to vemurafenib and continued MAPK signaling (FIG. 6B). In contrast, PAC-1 retains activity against A375VR with an $IC_{50}$ value of 2.4 µM (vs 1.2 µM for the parental cell line, FIG. 6C) and a similar $E_{max}$. We hypothesized that despite the inability of vemurafenib to inhibit ERK1/2 phosphorylation and MAPK signaling in the resistant A375VR cell line, the combination might retain partial capacity to exert a synergistic effect based on the PARP-1 cleavage observed for PAC-1+vemurafenib treatment, even under conditions of incomplete inhibition of ERK1/2 phosphorylation (FIG. 2E). To investigate if PAC-1 can re-sensitize A375VR cells to vemurafenib-induced apoptosis, A375VR cells were treated with PAC-1 in combination with low concentrations of vemurafenib. This combination treatment led to an increase in the proportion of cells undergoing apoptosis (FIG. 13A, 13C), indicating that the addition of PAC-1 can bypass the resistance mechanism of A375VR to vemurafenib. This effect was abolished when inactive variant PAC-1a was used (FIG. 13C). The PAC-1+ vemurafenib combination was synergistic, inducing an average of 7.5% higher population of apoptotic cells than predicted by the Bliss independence model (Bliss, *Ann Appl Biol* 1939; 26:585-615) (FIGS. 13A and 13B). Finally, to determine if PAC-1 can synergize with vemurafenib in vivo, A375VR cells were implanted subcutaneously in nude mice, and the mice were dosed daily for 15 days with vemurafenib (10 mg/kg), PAC-1 (100 mg/kg) or the combination. Treatment with vemurafenib or PAC-1 alone does not exert any antitumor affect in this in vivo model, while treatment with combination led to significant reduction in tumor volume compared to the untreated control (FIG. 6D).

Discussion. Given that the aberrations in the apoptotic signaling cascades in melanoma cells are upstream of the activation of procaspase-3, small molecules that directly activate procaspase-3 can induce apoptosis by bypassing the defective apoptotic circuitry. Activation of procaspase-3 with PAC-1 has been shown previously to have single agent efficacy against melanoma cells in culture (Wang et al., *Mol Oncol* 2014; 8:1640-52; Peterson et al., *Cancer Res* 2010; 70:7232-41; Putt et al., *Nat Chem Biol* 2006; 2:543-50), and now we show that PAC-1+vemurafenib, or PAC-1+vemurafenib+trametinib, are powerfully synergistic in the induction of caspase-3 activity and apoptotic cell death in melanomas with $^{V600E}$BRAF mutation. Besides melanomas, the $^{V600E}$BRAF mutation has been reported in several other cancers including Erdheim-Chester disease (ECD) (54%), Langerhans'-cell histiocytosis (LCH) (57%), non-small-cell lung cancer (NSCLC) (1.5%) and hairy-cell leukemia (100%). In two recent Phase II trials, efficacy of vemurafenib in several non-melanoma cancers harboring the $^{V600E}$BRAF mutation was reported, with promising results seen in patients with NSCLC, ECD, LCH and refractory hairy-cell leukemia. Given this clinical data and our current work showing potent synergy between PAC-1, vemurafenib, and trametinib in $^{V600E}$BRAF melanomas, these PAC-1/drug combinations can have efficacy in other malignancies harboring the $^{V600E}$BRAF mutation.

The $E_{max}$ parameter is a useful metric to assess the ability of a compound to quantitatively kill cancer cells in culture (Fallahi-Sichani et al., *Nat Chem Biol* 2013; 9:708-14). $E_{max}$ values less than 100% imply heterogeneity in the ability of the drug to kill the cancer cell population. Here we show that vemurafenib has an $E_{max}$ of ~97% in $^{V600E}$BRAF mutant A375 cells, but the $E_{max}$ value for PAC-1 approaches 100%. Because of this, no regrowth of A375 or SK-MEL-5 cells is observed in long-term experiments with PAC-1. However, extensive regrowth was observed in A375, UACC-62 and SK-MEL-5 cells treated only with vemurafenib for 20 days. With the addition of a low concentration of PAC-1 (1 µM) to vemurafenib, little to no regrowth was observed in cells. These results indicate that addition of low concentrations of PAC-1 (1 µM, a PAC-1 concentration that is readily achieved in vivo (Lucas et al., *Invest New Drugs* 2011; 29:901-11)) can be effective clinically in delaying resistance. The significant increase in caspase-3 activity, followed by massive induction of apoptosis early on during the combination treatment, likely kills off a large proportion of the cells that were initially insensitive to vemurafenib. Consequently, there is a significantly smaller residual population of cells that are unaffected by the treatment, crucial to delaying the regrowth of cells.

Currently, few options exist for patients who have developed vemurafenib-resistant melanomas. The MEK1/2 inhibitor, trametinib, though approved for melanomas with $^{V600E}$BRAF mutation, exerts limited activity in combination with BRAF inhibitor in patients who have failed prior therapy (Kim et al., *J Clin Oncol* 2013; 31:482-89). Our results show that PAC-1 still synergizes with vemurafenib to exert antitumor effects in vemurafenib-resistant tumors. Therefore, addition of PAC-1 might be a viable and alternative therapeutic option for patients whose melanomas have progressed after vemurafenib treatment. The PAC-1+ vemurafenib combination is well tolerated, has a good safety profile and exhibits significant antitumor effects in vivo. PAC-1 is currently in a Phase I clinical trial (NCT02355535), and both vemurafenib and trametinib are approved first-line treatment for $^{V600E}$BRAF melanoma. There is thus a clear path to translate the preclinical demonstration of synergy described in this work to clinical trials where this novel combination can be assessed in human patients with cancers harboring the $^{V600E}$BRAF mutation.

Materials and Methods

Cell culture and reagents. A375 (CRL-1619) and CHL-1 (CRL-9446) were purchased from ATCC on Nov. 5, 2014 and Nov. 18, 2014 respectively. A375SM was provided by Prof. Isiah Fidler (MD Anderson, Tex.) on Oct. 30, 2014. All cell lines except B16-F10, H460, and HCT 116 were cultured in DMEM supplemented with 10% FBS (Gemini). B16-F10, H460, and HCT 116 were cultured in RPMI with 10% FBS. Vemurafenib, trametinib and Annexin V-FITC (10040-02) were purchased from LC Laboratories, MedChemExpress, and SouthernBiotech respectively. The following antibodies were purchased from Cell Signalling Technology: anti-PARP-1 (9542), anti-caspase-3 (9662), anti-β-actin (4967), anti-phospho-ERK1/2 (Thr202/Tyr204) (4370), anti-ERK1/2 (4695) and anti-rabbit IgG HRP linked (7074). Anti-cleaved-PARP-1 (ab32561) antibody was purchased from Epitomics. PAC-1 and PAC-1a were synthesized as previously reported (Putt et al., *Nat Chem Biol* 2006; 2:543-50).

Cell line authentication. All human cell lines (A375, A375SM, CHL-1, H460, HCT 116, MIA PaCa-2, SK-MEL-5, and UACC-62) have been authenticated using the PowerPlex16HS Assay (Promega): 15 Autosomal Loci, X/Y at the University of Arizona Genetics Core. The results of the test and pherograms were recorded. *Mycoplasma* testing has been performed for the A375 cell line using the *Mycoplasma* detect PCR at the University of Illinois Veterinary Diagnostic Lab.

Cellular proliferation assays. 1000-2000 cells were seeded per well in a 96-well plate and allowed to adhere before DMSO solutions of PAC-1 or vemurafenib were added to each well. Proliferation was assessed by the sulforhodamine B (SRB) assay.

Annexin V/PI flow cytometry analysis. 70,000 cells were seeded in 12-well plates and allowed to adhere before addition of compounds. Cells were treated with compounds for 24 h at 37° C., after which they were harvested and resuspended in 450 μL of cold buffer (10 mM HEPES, 140 mM NaCl, 2.5 mM CaCl$_2$ pH 7.4) premixed with Annexin V-FITC and PI (0.55 μg/mL) dyes. Samples were analyzed on a BD Biosciences LSR II flow cytometer and data analysis was performed using FCS Express V3-2.

Caspase-3/7 activity assay. 5,000-8,000 cells were plated in 96 well plates and allowed to adhere. Cells were treated with 1 μM of staurosporine for 24 h or with 13 μM of raptinal (Palchaudhuri et al., *Cell Rep* 2015; 13:2027-36) for 3 h as positive control, DMSO as negative control and indicated concentrations of PAC-1 and vemurafenib for 0, 2, 4, 7, 10, 12, 16, 20 or 24 h. Plates were then assessed for caspase-3/7 activity via addition of bifunctional lysis and activity buffer (200 mM HEPES, 400 mM NaCl, 40 mM DTT, 0.4 mM EDTA, 1% Triton-X, pH 7.4) with 20 μM of Ac-DEVD-AFC (Cayman Chemicals) as the fluorogenic substrate ($\lambda_{ex}$=400 nm, $\lambda_{em}$=505 nm). Plates were preincubated at 37° C. at 30 min in the Synergy multi-mode reader (BioTek) then read for 30 min at 3 min intervals. The slopes for each well were calculated. Activity is expresses as normalized to minimal and maximal activity observed within the assay.

In vitro resistance assay. 800 A375 or UACC-62 cells were plated in 96-well plates and allowed to attach overnight. The next day, vemurafenib (5 or 10 μM) or PAC-1 (1 μM) were treated in six technical replicates for 5, 10 and 20 days. Fresh media and compounds were added every 2-3 days for the duration of the study. At the end of 5, 10 or 20 days, the wells were fixed with 10% cold trichloroacetic acid for 1 h at 4° C. The wells were then washed, allowed to dry and stained with 0.5% SRB dye for 30 min at room temperature. The wells were then washed with 0.1% acetic acid and allowed to dry. At this point, images of the plates were taken with GelDoc XR (BioRad). Finally, 200 μL of 10 mM Tris base (pH >10.4) was added into well and the absorbance at 510 nm were read using SpectraMax Plus (Molecular Devices). The absorbance at 510 nm is plotted against the days post treatment as an indication of cell proliferation over the time course of the experiment.

Immunoblotting. Cells and tumor tissues were lysed using RIPA buffer containing phosphatase and protease inhibitor cocktail (Calbiochem). The protein concentration of each sample was determined by the BCA assay (Pierce). Cell lysates containing 20 μg of protein was loaded into each lane of 4-20% gradient gels (BioRad) for SDS-PAGE. Proteins were transferred onto PDVF membrane for Western blot analysis.

PCR and sequencing. A375 and A375VR cells were lysed and RNA extracted using the RNeasy kit (Qiagen). 900 ng of RNA was used for reverse transcription reaction using iScript cDNA synthesis kit (BioRad). qPCR reactions were ran on the 7900HT fast real-time PCR system (Applied Biosystems). Regular PCR reactions were ran using the MyFi Mix PCR kit (Bioline) for 35 cycles and ran on a 1% agarose gel. Target amplicons were gel extracted and sequenced at the UIUC core sequencing facility. Primers used can be found in the following table.

| Primer sequences used to characterize vemurafenib-resistant A375VR. | | |
|---|---|---|
| MDR1 F | ACACCATGGGGAAGGTGAAG | (SEQ ID NO: 1) |
| MDR1 R | GTGACCAGGCGCCCAATA | (SEQ ID NO: 2) |
| GAPDH F | ACACCATGGGGAAGGTGAAG | (SEQ ID NO: 3) |
| GAPDH R | GTGACCAGGCGCCCAATA | (SEQ ID NO: 4) |
| BRAF F | GGCTCTCGGTTATAAGATGGC | (SEQ ID NO: 5) |
| BRAF R | ACAGGAAACGCACCATATCC | (SEQ ID NO: 6) |
| MEK1 Amp F | CGTTACCCGGGTCCAAAATG | (SEQ ID NO: 7) |
| MEK1 Amp R | CTTTGTCACAGGTGAAATGC | (SEQ ID NO: 8) |
| MEK1 Seq F | CATGGATGGAGGTTCTCTGG | (SEQ ID NO: 9) |
| MEK1 Seq R | AGGGCTTGACATCTCTGTGC | (SEQ ID NO: 10) |
| MEK2 Amp F | CTCCCGGCCCGCCCCTATG | (SEQ ID NO: 11) |
| MEK2 Amp R | GTGGAGGCGCCAGCCTGTCC | (SEQ ID NO: 12) |
| MEK2 Seq F | GTCAGCATCGCGGTTCTCC | (SEQ ID NO: 13) |
| MEK2 Seq R | TCACCCCGAAGTCACACAG | (SEQ ID NO: 14) |
| NRAS F | AGCTTGAGGTTCTTGCTGGT | (SEQ ID NO: 15) |

-continued

| Primer sequences used to characterize vemurafenib-resistant A375VR. | | |
|---|---|---|
| NRAS R | TCAGGACCAGGGTGTCAGTG | (SEQ ID NO: 16) |
| AKT1 F | AGCGCCAGCCTGAGAGGA | (SEQ ID NO: 17) |
| AKT1 Amp R | TCTCCATCCCTCCAAGCTAT | (SEQ ID NO: 18) |
| AKT1 Seq R | GACAGGTGGAAGAACAGCT | (SEQ ID NO: 19) |

A375 and A375VR xenograft model. All animal studies were performed in accordance with UIUC IACUC guidelines (protocol no. 14292). 0.1 mL of A375 or A375VR in 1:1 DMEM:matrigel (Corning) was injected into the right flank of 6-7 (A375) or 5 (A375VR) week old female athymic nude mice (Charles River). In the both models, the mice were randomized into four groups: control, 100 mg/kg PAC-1, 10 mg/kg vemurafenib, and the combination of 100 mg/kg PAC-1 and 10 mg/kg vemurafenib (n=8). Initial tumor volume measurements were taken and dosing was initiated for a period of 15 days. Vemurafenib was formulated as 5% DMSO in 1% methyl cellulose and given twice daily by oral gavage (p.o.). PAC-1 was formulated in 200 mg/mL hydroxypropyl-β-cyclodextrin at pH 5.5 and given by intraperitoneal (i.p.) injection. Tumor length and width measurements were taken three times a week and volume was calculated as $0.52*L*W^2$. At the end of the study, the mice were euthanized and tumors were excised. The tumors were weighed and used for Western blot and immunohistochemistry.

Immunohistochemistry of A375 tumors and quantification of Ki-67 index.
Immunohistochemistry (IHC) was performed on 4 μm-thick formalin-fixed paraffin-embedded A375 tumors after H&E staining confirmed the presence of a neoplastic cell population along with adequate tissue integrity. Antibody against Ki-67 (Biocare Medical #CRM325) was used for IHC and staining was visualized using the IntelliPATH FLX DAB chromogen kit (Biocare Medical #IPK 5010 G80). Human tonsil was used as the positive control tissue. Polymer negative control serum (mouse and rabbit) (Biocare Medical #NC499) was substituted for the primary antibody as a negative control. For quantification of Ki-67 index, 2000 neoplastic cells were counted and the percentage of positive cells was calculated. In tumors too small to quantify 2000 cells, the maximal number of neoplastic cells were counted. All slides were reviewed by a single veterinary pathologist.

Example 2

Pharmaceutical Dosage Forms

The following formulations illustrate representative pharmaceutical dosage forms that may be used for the therapeutic or prophylactic administration of the combination compounds described herein (e.g., PAC-1 and the second active agent), or pharmaceutically acceptable salts or solvates thereof (hereinafter referred to as 'Compounds X', which can be one active agent or a combination of two active agents):

| (i) Tablet 1 | mg/tablet |
|---|---|
| 'Compounds X' | 200.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 400.0 |

| (ii) Tablet 2 | mg/tablet |
|---|---|
| 'Compounds X' | 120.0 |
| Microcrystalline cellulose | 410.0 |
| Starch | 50.0 |
| Sodium starch glycolate | 15.0 |
| Magnesium stearate | 5.0 |
| | 600.0 |

| (iii) Capsule | mg/capsule |
|---|---|
| 'Compounds X' | 110.0 |
| Colloidal silicon dioxide | 1.5 |
| Lactose | 465.5 |
| Pregelatinized starch | 120.0 |
| Magnesium stearate | 3.0 |
| | 700.0 |

| (iv) Injection 1 (1 mg/mL) | mg/mL |
|---|---|
| 'Compounds X' | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compounds X' | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compounds X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient(s) 'Compounds X'. Aerosol formulation (vi) may be used in conjunction with a standard, metered dose aerosol dispenser. Additionally, the specific ingredients and proportions are for illustrative purposes. Ingredients may be exchanged for suitable equivalents (e.g., components described above) and proportions may be varied, according to the desired properties of the dosage form of interest.

Example 3

Tablet Forms

The following formulation illustrates representative pharmaceutical dosage forms that may be used for the therapeutic or prophylactic administration of the combination compounds described herein (e.g., PAC-1 and the second active agent), or pharmaceutically acceptable salts or solvates thereof:

| (i) Tablet A | mg/tablet |
|---|---|
| PAC-1 | 250.0 |
| Microcrystalline cellulose | 127.5 |
| Mannitol | 50.0 |
| Sodium starch glycolate | 50.0 |
| Fumed silica | 2.5 |
| Hydroxypropyl cellulose | 15.0 |
| Sodium stearyl fumarate | 5.0 |
| | 500.0 |

| (ii) Tablet B | mg/tablet |
|---|---|
| Second agent | 250.0 |
| Microcrystalline cellulose | 127.5 |
| Mannitol | 50.0 |
| Sodium starch glycolate | 50.0 |
| Fumed silica | 2.5 |
| Hydroxypropyl cellulose | 15.0 |
| Sodium stearyl fumarate | 5.0 |
| | 500.0 |

The second agent can be, for example, vemurafenib, dabrafenib, BMS-908662 (also known as XL281), encorafenib (LGX818), PLX3603 (RO5212054), or RAF265 (1-methyl-5-[2-[5-(trifluoromethyl)-1H-imidazol-2-yl]pyridin-4-yl]oxy-N-[4-(trifluoromethyl)phenyl]-benzimidazol-2-amine). The second agent can also be a MEK inhibitor, or a combination of a MEK inhibitor and one of the aforementioned actives. Furthermore, a third pharmaceutical dosage form similar to Tablet B can be used to administer the MEK inhibitor (e.g., as a third, separate, and sequential administration of an active). These formulations may be prepared by conventional procedures well known in the pharmaceutical art. It will be appreciated that the above pharmaceutical compositions may be varied according to well-known pharmaceutical techniques to accommodate differing amounts and types of the active agents. Additionally, the specific ingredients and proportions are for illustrative purposes. Ingredients may be exchanged for suitable equivalents (e.g., components described above) and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A composition comprising:
   (a) the compound PAC-1:

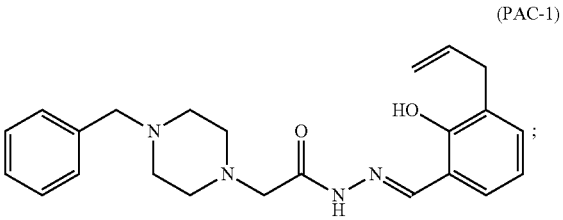 [SMILES: C=CCc1cccc(/C=N/NC(=O)CN2CCN(Cc3ccccc3)CC2)c1O]

(PAC-1)

(b) a second active agent, which agent is an inhibitor of the BRAF enzyme having a mutation, wherein the second active agent is vemurafenib and the concentration of vemurafenib is about 0.5 µM to about 30 µM; and
   (c) a pharmaceutically acceptable diluent, excipient, or carrier;
   wherein the concentration of PAC-1 is about 4 µM to about 12 µM.

2. The composition of claim 1 wherein vemurafenib is an inhibitor of the BRAF enzyme that has the V600E or the V600K mutation.

3. The composition of claim 1 wherein the composition further comprises a MEK inhibitor.

4. The composition of claim 1 wherein the carrier comprises water, a buffer, a sugar, a cellulose, a cyclodextrin, or a combination thereof.

* * * * *